(12) United States Patent
Ataman-Onal et al.

(10) Patent No.: US 10,465,012 B2
(45) Date of Patent: Nov. 5, 2019

(54) BIORESORBABLE NONLAMELLAR MICROPARTICLES AND USES THEREOF

(71) Applicant: CENTRE NATIONAL DE LA RECHERCHE SCIENTIFIQUE (C.N.R.S.), Paris (FR)

(72) Inventors: Yasemin Ataman-Onal, Lyons (FR); Thierry Delair, Echalas (FR); Genevieve Inchauspe, Lyons (FR); Pascale Jeannin, Bouchemaine (FR); Glaucia Paranhos-Baccala, Lyons (FR); Bernard Verrier, Mornant (FR)

(73) Assignee: CENTRE NATIONAL DE LA RECHERCHE SCIENTIFIQUE (C.N.R.S.), Paris (FR)

( * ) Notice: Subject to any disclaimer, the term of this patent is extended or adjusted under 35 U.S.C. 154(b) by 291 days.

(21) Appl. No.: 13/739,421

(22) Filed: Jan. 11, 2013

(65) Prior Publication Data

US 2013/0164250 A1 Jun. 27, 2013

Related U.S. Application Data

(60) Division of application No. 12/081,296, filed on Apr. 14, 2008, now Pat. No. 8,377,477, which is a continuation of application No. 10/570,948, filed as application No. PCT/FR2004/050447 on Sep. 21, 2004, now abandoned.

(30) Foreign Application Priority Data

Sep. 22, 2003 (FR) ..................... 0311057

(51) Int. Cl.
| | | |
|---|---|---|
| A61K 47/69 | (2017.01) | |
| A61K 9/16 | (2006.01) | |
| A61K 9/51 | (2006.01) | |
| A61K 47/34 | (2017.01) | |
| G01N 33/543 | (2006.01) | |
| C07K 14/005 | (2006.01) | |
| C07K 16/10 | (2006.01) | |
| C07K 16/40 | (2006.01) | |
| A61K 47/48 | (2006.01) | |
| A61K 39/00 | (2006.01) | |

(52) U.S. Cl.
CPC .............. C07K 16/40 (2013.01); A61K 9/167 (2013.01); A61K 9/5153 (2013.01); A61K 9/5192 (2013.01); A61K 47/34 (2013.01); A61K 47/482 (2013.01); A61K 47/6935 (2017.08); C07K 14/005 (2013.01); C07K 16/1054 (2013.01); C07K 16/1072 (2013.01); G01N 33/54346 (2013.01); A61K 39/00 (2013.01); A61K 2039/6093 (2013.01); C12N 2740/16222 (2013.01); C12N 2740/16322 (2013.01); C12N 2770/24222 (2013.01)

(58) Field of Classification Search
None
See application file for complete search history.

(56) References Cited

U.S. PATENT DOCUMENTS

| 5,662,938 A | 9/1997 | Vert et al. |
|---|---|---|
| 6,346,375 B1 | 2/2002 | Chien |
| 2008/0241259 A1 | 10/2008 | Ataman-Onal et al. |

FOREIGN PATENT DOCUMENTS

| WO | WO 1992/013567 | | 8/1992 |
|---|---|---|---|
| WO | WO 93/00365 | | 1/1993 |
| WO | WO 93/25191 | | 12/1993 |
| WO | WO 97/02810 A | | 1/1997 |
| WO | WO 98/33487 A | | 8/1998 |
| WO | WO 00/06123 A | | 2/2000 |
| WO | WO 01/26681 | | 4/2001 |
| WO | WO 2003/070909 | * | 8/2003 |

OTHER PUBLICATIONS

Gautier et al., Journal of Biomaterial Science—Polymer Edition, 2001, 12(4):429-450.*
Govender et al., Journal of Controlled Release, 1999, 57:171-185.*
Eldridge, J.H., et al.; "Biodegradable and Biocompatible Poly (DL-Lactide-Co-Glycolide) Microspheres as an Adjuvant for Staphylococcal Enterotoxin B Toxoid Which Enhances the Level of Toxin-Neutralizing Antibodies;" Infection and Immunity; vol. 59, No. 9, pp. 2978-2986, Sep. 1991.
Hermanson, G.T.; "Bioconjugate Techniques;" Academic Press; 1996.
Jeon, H.J., et al; "Effect of solvent on the preparation of surfactant-free poly (DL-lactide-co-glycolide) nanoparticles and norfloxacin release characteristics;" International Journal of Pharmaceutics; 2000, 207, pp. 99-108.
Kohler, G., et al.; "Continuous cultures of fused cells secreting antibody of predefined specificity;" MRC Laboratory of Molecular Biology; vol. 256, pp. 495-497, Aug. 7, 1975.
Kohler, G., et al.; "Derivation of specific antibody-producing tissue culture and tumor lines by cell fusion;" MRC Laboratory of Molecular Biology; vol. 6, pp. 511-519, 1976.
Kovacsovics-Bankowski, M., et al.; "Efficient major histocompatibiltiy comlex class I presentation of exogenous antigen upon phagocytosis by macrophages;" Proc. Natl. Acad. Sci. USA; vol. 90, pp. 4942-4946, Jun. 1993.
Lundblad, R.L., Ph.D.; "Chemical Reagents for Protein Modification;" CRC Press, Inc.; (1991). (contents only).
Moore, A., et al.; "Immunization with a soluble recombinant HIV protein entrapped in biodegradable microparticles induces HIV-specific CD8+ cytotoxic T lymphocytes and CD4+ Th1 cells;" Vaccine; vol. 13, No. 18; pp. 1741-1749 (1995).

(Continued)

Primary Examiner — Nicole Kinsey White
(74) Attorney, Agent, or Firm — Oliff PLC

(57) ABSTRACT

Nonlamellar bioresorbable microparticles to which protein substances are bonded, and a method for preparing the microparticles, comprising: (i) preparing the microparticles from at least one bioresorbable polymer without stabilizer and without surfactant; and (ii) bonding the protein substances to the microparticles obtained in step (i) without surfactant.

8 Claims, 8 Drawing Sheets

Figure 2:
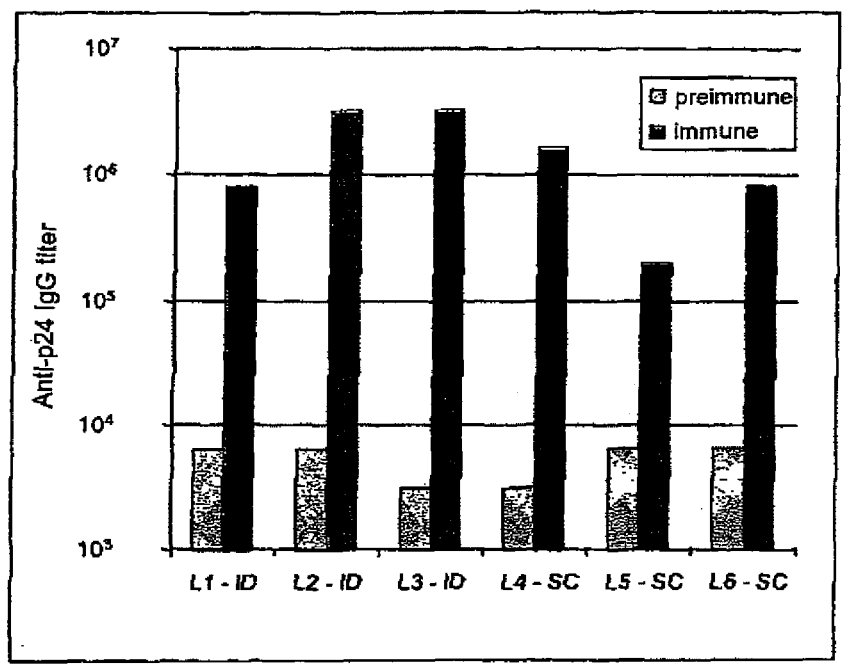

Specification includes a Sequence Listing.

(56) References Cited

OTHER PUBLICATIONS

Nab, J. W., et al.; "Clonazepam Release from Poly (DL-lactide-co-glycolide) Nanoparticles Prepared by Dialysis Method;" Arch. Pharm. Res.; vol. 21, No. 4; pp. 418-422 (1998).

Vordermeier, H.M., et al.; "Synthetic delivery system for tuberculosis vaccines: immunological evaluation of the M. tuberculosis 38 kDa protein entrapped in biodegradable PLG micropaarticles;" Vaccine; vol. 13, No. 16; pp. 1576-1582 (1995).

English translation of Nov. 30, 2010 Japanese Office Action issued in Japanese Patent Application No. 2006-526671 (Received on Dec. 7, 2010).

Jeong et al., "Preparation of Poly(DL-lactide-co-glycolide) Nanoparticles Without Surfactant," *Journal of Applied Polymer Science*, 2001, vol. 80, pp. 2228-2236.

Arribillaga et al., "Vaccination with an adenoviral vector encoding hepatitis C virus (HCV) NS3 protein protects against infection with HCV-recombinant vaccinia virus," *Vaccine*, 2002, vol. 21, pp. 202-210.

Nam et al., "Intracellular drug delivery using poly(D,L-lactide-co-glycolide) nanoparticles derivatized with a peptide from a transcriptional activator protein of HIV-1," *Biotechnology Letters*, 2002, vol. 24, pp. 2093-2098.

Kazzaz et al., "Novel anionic microparticles are a potent adjuvant for the induction of cytotoxic T lymphocytes against recombinant p55 gag from HIV-1," *Journal of Controlled Release*, 2000, vol. 67, pp. 347-356.

Ogawa et al., "A New Technique to Efficiently Entrap Leuprolide Acetate into Microcapsules of Polylactic Acid or Copoly(Lactic/Glycolic) Acid," *Chem. Pharm. Bill.*, 1988, 36(3), 1095-1103.

Otten et al., Journal of Virology, May 2003, 77(10):6087-6092.
Dawson et al., Pharmaceutical Research, 2000, 17(11): 1420-1425.
Maruyama et al., Bioconjugate Chem., 1997, 8:735-742.
Jeong et al., Colloids and Surfaces B: Bionterfaces, 2000, 18:371-379.
Sun et al., Arch. Pharm. Res., 2003, 26(6):504-510.
Woodberry et al., Journal of Virology, 1999, 73(7):5320-5325.
Sep. 17, 2009 Office Action issued in U.S. Appl. No. 12/081,296.
Mar. 16, 2010 Office Action issued in U.S. Appl. No. 12/081,296.
Aug. 5, 2010 Office Action issued in U.S. Appl. No. 12/081,296.
Jan. 19, 2011 Office Action issued in U.S. Appl. No. 12/081,296.
Oct. 17, 2011 Office Action issued in U.S. Appl. No. 12/081,296.
Apr. 26, 2012 Office Action issued in U.S. Appl. No. 12/081,296.

Delphine Lamalle-Bernard et al., "Coadsorption of HIV-1 p24 and gp120 proteins to surfactant-free anionic PLA nanoparticles preserves antigenicity and immunogenicity," Journal of Controlled Release 115 (2006), pp. 57-67.

Christophe Guillon et al., "Formulation of HIV-1 Tat and p24 antigens by PLA nanoparticles or MF59 impacts the breadth, but not the magnitude, of serum and faecal antibody responses in rabbits," Vaccine 25 (2007) pp. 7491-7501.

Vincent Pavot et al., "Encapsulation of Nod1 and Nod2 receptor ligands into poly(lactic acid) nanoparticles potentiates their immune properties," Journal of Controlled Release 167 (2013) pp. 60-67.

Fiorenza Rancan et al., "Particle-based transcutaneous administration of HIV-1 p. 24 protein to human skin explants and targeting of epidermal antigen presenting cells," Journal of Controlled Release 176 (2014) pp. 115-122.

\* cited by examiner

Figure 1
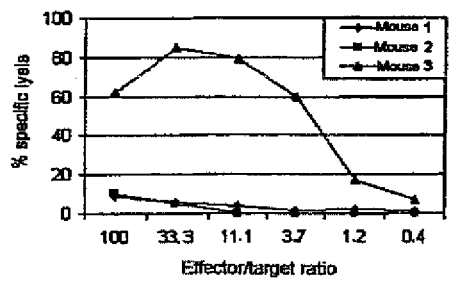
Figure 1A
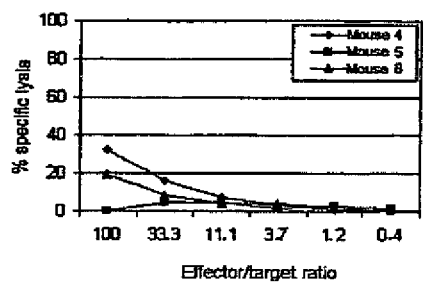
Figure 1B
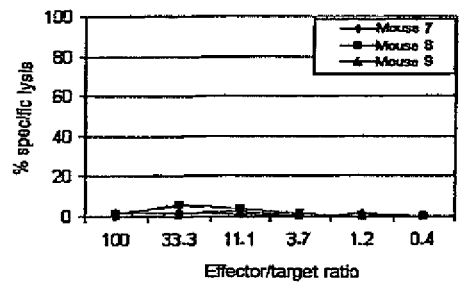
Figure 1C
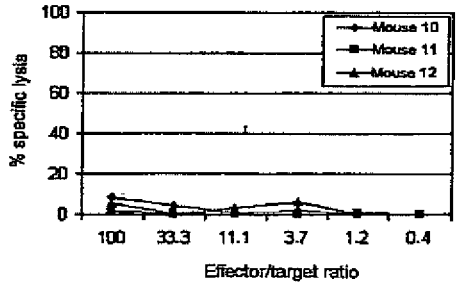
Figure 1D
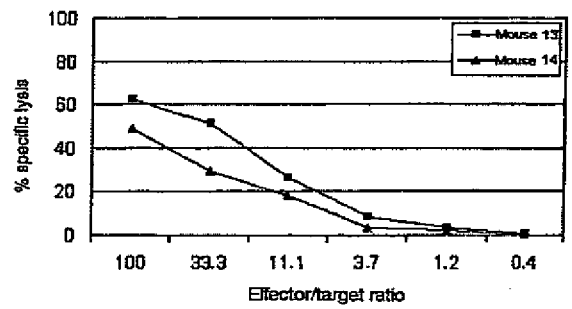
Figure 1E

SEQUENCE LISTING

```
<160> NUMBER OF SEQ ID NOS: 32

<210> SEQ ID NO 1
<211> LENGTH: 101
<212> TYPE: PRT
<213> ORGANISM: HIV

<400> SEQUENCE: 1

Met Glu Pro Val Asp Pro Arg Leu Glu Pro Trp Lys His Pro Gly Ser
1               5                   10                  15

Gln Pro Arg Thr Ala Cys Thr Asn Cys Tyr Cys Lys Lys Cys Cys Phe
            20                  25                  30

His Cys Gln Val Cys Phe Ile Arg Lys Ala Leu Gly Ile Ser Tyr Gly
        35                  40                  45

Arg Lys Lys Arg Arg Gln Arg Arg Ala Pro Gln Asp Ser Glu Thr
    50                  55                  60

His Gln Val Ser Pro Pro Lys Gln Pro Ala Ser Gln Pro Arg Gly Asp
65                  70                  75                  80

Pro Thr Gly Pro Lys Glu Ser Lys Lys Lys Val Glu Arg Glu Thr Glu
                85                  90                  95

Thr His Pro Val Asn
            100

<210> SEQ ID NO 2
<211> LENGTH: 288
<212> TYPE: PRT
<213> ORGANISM: HCV

<400> SEQUENCE: 2

Met Arg Gly Ser His His His His His His Gly Ser Val Asp Glu Ser
1               5                   10                  15

Met Asp Glu Phe Ala Val Asp Phe Ile Pro Val Glu Asn Leu Glu Thr
            20                  25                  30

Thr Met Arg Ser Pro Val Phe Ser Asp Asn Ser Ser Pro Pro Ala Val
        35                  40                  45

Pro Gln Ser Tyr Gln Val Ala His Leu His Ala Pro Thr Gly Ser Gly
    50                  55                  60

Lys Ser Thr Lys Val Pro Ala Ala Tyr Ala Ala Gln Gly Tyr Lys Val
65                  70                  75                  80

Leu Val Leu Asn Pro Ser Val Ala Ala Thr Leu Gly Phe Gly Ala Tyr
                85                  90                  95

Met Ser Lys Ala His Gly Ile Asp Pro Asn Ile Arg Thr Gly Val Arg
                100                 105                 110
```

-continued

```
Thr Ile Thr Thr Gly Ser Pro Ile Thr Tyr Ser Tyr Gly Lys Phe
        115                 120                 125
Leu Ala Asp Gly Gly Cys Ser Gly Gly Ala Tyr Asp Ile Ile Cys
    130                 135                 140
Asp Glu Cys His Ser Thr Asp Ala Thr Ser Ile Leu Gly Ile Gly Thr
145                 150                 155                 160
Val Leu Asp Gln Ala Glu Thr Ala Gly Ala Arg Leu Thr Val Leu Ala
                165                 170                 175
Thr Ala Thr Pro Pro Gly Ser Val Thr Val Pro His Pro Asn Ile Glu
            180                 185                 190
Glu Val Ala Leu Ser Thr Thr Gly Glu Ile Pro Phe Tyr Gly Lys Ala
                195                 200                 205
Ile Pro Leu Glu Ala Ile Lys Gly Gly Arg His Leu Ile Phe Cys His
    210                 215                 220
Ser Lys Lys Lys Cys Asn Glu Leu Ala Ala Lys Leu Val Ala Leu Gly
225                 230                 235                 240
Val Asn Ala Val Ala Tyr Tyr Arg Gly Leu Asp Val Ser Val Ile Pro
                245                 250                 255
Thr Ser Gly Asp Val Val Val Ala Thr Asp Ala Leu Met Thr Gly
            260                 265                 270
Phe Thr Gly Asp Phe Asp Ser Val Ile Asp Cys Asn Thr Cys Val Ile
        275                 280                 285
```

<210> SEQ ID NO 3
<211> LENGTH: 9
<212> TYPE: PRT
<213> ORGANISM: HIV

<400> SEQUENCE: 3

```
Ala Met Gln Met Leu Lys Glu Thr Ile
1               5
```

<210> SEQ ID NO 4
<211> LENGTH: 15
<212> TYPE: PRT
<213> ORGANISM: HIV

<400> SEQUENCE: 4

```
Cys Phe His Cys Gln Val Cys Phe Thr Lys Lys Gly Leu Gly Ile
1               5                   10                  15
```

<210> SEQ ID NO 5
<211> LENGTH: 15
<212> TYPE: PRT
<213> ORGANISM: HIV

<400> SEQUENCE: 5

```
Val Cys Phe Thr Lys Lys Gly Leu Gly Ile Ser Tyr Gly Arg Lys
1               5                   10                  15
```

<210> SEQ ID NO 6
<211> LENGTH: 15
<212> TYPE: PRT
<213> ORGANISM: HIV

<400> SEQUENCE: 6

```
Lys Gly Leu Gly Ile Ser Tyr Gly Arg Lys Lys Arg Arg Gln Arg
1               5                   10                  15
```

-continued

```
<210> SEQ ID NO 7
<211> LENGTH: 15
<212> TYPE: PRT
<213> ORGANISM: HIV

<400> SEQUENCE: 7

Ser Tyr Gly Arg Lys Lys Arg Arg Gln Arg Arg Ser Pro Gln
1               5                   10                  15

<210> SEQ ID NO 8
<211> LENGTH: 15
<212> TYPE: PRT
<213> ORGANISM: HIV

<400> SEQUENCE: 8

Lys Arg Arg Gln Arg Arg Ser Pro Gln Asp Ser Glu Thr His
1               5                   10                  15

<210> SEQ ID NO 9
<211> LENGTH: 15
<212> TYPE: PRT
<213> ORGANISM: HIV

<400> SEQUENCE: 9

Arg Arg Ser Pro Gln Asp Ser Glu Thr His Gln Val Ser Leu Ser
1               5                   10                  15

<210> SEQ ID NO 10
<211> LENGTH: 2838
<212> TYPE: DNA
<213> ORGANISM: HCV

<400> SEQUENCE: 10
gcgcctatca cggcctattc ccaacaaacg cggggcctgc ttggctgtat catcactagc        60
ctcacaggtc gggacaagaa ccaggtcgat ggggaggttc aggtgctctc caccgcaacg       120
caatctttcc tggcgacctg cgtcaatggc gtgtgttgga ccgtctacca tggtgccggc       180
tcgaagaccc tggccggccc gaagggtcca atcacccaaa tgtacaccaa tgtagaccag       240
gacctcgtcg ctggccggc gccccccggg gcgcgctcca tgacaccgtg cacctgcggc       300
agctcggacc tttacttggt cacgaggcat gccgatgtca ttccggtgcg ccggcgaggc       360
gacagcaggg ggagtctact ctcccctagg cccgtctcct acctgaaggg ctcctcgggt       420
ggaccactgc tttgcccttc ggggcacgtt gtaggcatct ccggctgc tgtgtgcacc        480
cgggggggttg cgaaggcggt ggacttcata cccgttgagt ctatggaaac taccatgcgg       540
tctccggtct tcacagacaa ctcatcccct ccggccgtac cgcaaacatt ccaagtggca       600
catttacacg ctcccactgg cagcggcaag agcaccaaag tgccggctgc atatgcagcc       660
caagggtaca aggtgcgcgt cctaaacccg tccgttgctg ccacattggg ctttggagcg       720
tatatgtcca aggcacatgg catcgagcct aacatcagaa ctgggggtaag gaccatcacc       780
acgggcggcc ccatcacgta ctccacctat ggcaagttcc ttgccgacgg tggatgctcc       840
gggggcgcct atgacatcat aatatgtgac gaatgccact caactgactg acaaccatc       900
ttgggcatcg gcagtcct ggatcaggca gagacggctg gagcgcggct cgtcgtgctc         960
gccaccgcca cgcctccggg atcgatcacc gtgccacacc caacatcga ggaagtggcc       1020
ctgtccaaca ctgggagat tcccttctat ggcaaagcca tcccattga ggccatcaag       1080
ggggaaggc atctcatctt ctgccattcc aagaagaagt gtgacgagct cgccgcaaag       1140
ctgacaggcc tcggactcaa cgctgtagcg tattacaggg gtctcgatgt gtccgtcata       1200
```

-continued

```
ccgactagcg gagacgtcgt tgtcgtggca acagacgctc taatgacggg ctttaccggc   1260
gactttgact cagtgatcga ctgcaacaca tgtgtcaccc agacagtcga tttcagcttg   1320
gatcccacct tcaccattga gacgaccacc gtgccccaag acgcggtgtc gcgctcgcag   1380
cggcgaggta ggactggcag gggcaggagt ggcatctaca ggtttgtgac tccaggagaa   1440
cggccctcag gcatgttcga ctcctcggtc ctgtgtgagt gctatgacgc aggctgcgct   1500
tggtatgagc tcacgcccgc tgagactaca gtcaggttgc gggcttacct gaatacacca   1560
gggttgcccg tctgccagga ccatctggag ttctgggaaa gcgtcttcac aggcctcacc   1620
cacatagatg cccacttcct gtcccaaacc aagcaggcag gagacaactt cccctacctg   1680
gtggcatacc aagccacggt gtgcgccagg gctcaggctc acctccatc gtgggatcaa    1740
atgtggaagt gtctcatacg gcttaaacct acgctgcacg gccaacacc cctgctgtat    1800
aggctaggag ccgttcaaaa tgagatcacc ctcacacatc ccataaccaa attcgtcatg   1860
gcatgcatgt cggccgacct ggaggtcgtc actagcacct gggtgctggt aggcggagtc   1920
cttgcagctc tggccgcata ttgcctgaca accggtagtg tggtcattgt gggtaggatc   1980
attttgtccg ggaggccggc tgttgttccc gacaggggaag tcctctaccg ggagttcgat   2040
gaaatggaag agtgcgcctc acacctccct tacatcgagc aaggaatgca gctcgccgag   2100
cagttcaagc agaaggcact cgggttgctg caaacagcca ccaagcaagc ggaggccgct   2160
gctcccgtgg tggagtccag gtggcgggcc cttgaggcct ctgggcaaa gcacatgtgg   2220
aacttcatca ccgggataca gtacttagca ggcttatcca ctctgcctgg gaaccccgcg   2280
atagcatcac tgatggcatt cacagcctct atcaccagtc cgctcaccac ccagaatacc   2340
ctcctattca acatcttagg gggatgggtg gctgctcaac tcgctcctcc cagtgctgct   2400
tcggccttcg tgggtgccgg cattgccggt gcggccattg gcagcatagg ccttgggaag   2460
gtgcttgtgg acattctggc gggctatgga gcggggtgg ccggtgcact cgtggctttt   2520
aaggtcatga gcggcgaggc gccctccgcc gaggacctgg ttaacttgct ccctgccatc   2580
ctctcccccg gcgccttggt cgtcgggatc gtgtgtgcag caatcctgcg tcggcacgtg   2640
ggcccgggag aggggctgt gcagtggatg aaccggctga tagcgttcgc ttcgcggggt   2700
aaccacgttt ccccccacgca ctacgtgcct gagagcgacg ccgcagcacg tgtaactcag   2760
atcctctcca gcctcaccat cactcagctg ctgaagaggc ttcaccagtg gattaatgag   2820
gactgctcca cgccatgc                                                  2838
```

<210> SEQ ID NO 11
<211> LENGTH: 10
<212> TYPE: PRT
<213> ORGANISM: HCV

<400> SEQUENCE: 11

Lys Leu Val Ala Leu Gly Val Asn Ala Val
1               5                   10

<210> SEQ ID NO 12
<211> LENGTH: 15
<212> TYPE: PRT
<213> ORGANISM: HIV

<400> SEQUENCE: 12

Glu Gln Ile Gly Trp Met Thr Asn Asn Pro Pro Ile Pro Val Gly
1               5                   10                  15

```
<210> SEQ ID NO 13
<211> LENGTH: 15
<212> TYPE: PRT
<213> ORGANISM: HIV

<400> SEQUENCE: 13

Trp Met Thr Asn Asn Pro Pro Ile Pro Val Gly Glu Ile Tyr Lys
1               5                   10                  15

<210> SEQ ID NO 14
<211> LENGTH: 15
<212> TYPE: PRT
<213> ORGANISM: HIV

<400> SEQUENCE: 14

Asn Pro Pro Ile Pro Val Gly Glu Ile Tyr Lys Arg Trp Ile Ile
1               5                   10                  15

<210> SEQ ID NO 15
<211> LENGTH: 15
<212> TYPE: PRT
<213> ORGANISM: HIV

<400> SEQUENCE: 15

Pro Val Gly Glu Ile Tyr Lys Arg Trp Ile Ile Leu Gly Leu Asn
1               5                   10                  15

<210> SEQ ID NO 16
<211> LENGTH: 15
<212> TYPE: PRT
<213> ORGANISM: HIV

<400> SEQUENCE: 16

Ile Tyr Lys Arg Trp Ile Ile Leu Gly Leu Asn Lys Ile Val Arg
1               5                   10                  15

<210> SEQ ID NO 17
<211> LENGTH: 15
<212> TYPE: PRT
<213> ORGANISM: HIV

<400> SEQUENCE: 17

Trp Ile Ile Leu Gly Leu Asn Lys Ile Val Arg Met Tyr Ser Pro
1               5                   10                  15

<210> SEQ ID NO 18
<211> LENGTH: 15
<212> TYPE: PRT
<213> ORGANISM: HIV

<400> SEQUENCE: 18

Gly Leu Asn Lys Ile Val Arg Met Tyr Ser Pro Thr Ser Ile Leu
1               5                   10                  15

<210> SEQ ID NO 19
<211> LENGTH: 15
<212> TYPE: PRT
<213> ORGANISM: HIV

<400> SEQUENCE: 19

Ile Val Arg Met Tyr Ser Pro Thr Ser Ile Leu Asp Ile Arg Gln
1               5                   10                  15
```

<210> SEQ ID NO 20
<211> LENGTH: 15
<212> TYPE: PRT
<213> ORGANISM: HIV

<400> SEQUENCE: 20

Tyr Ser Pro Thr Ser Ile Leu Asp Ile Arg Gln Gly Pro Lys Glu
1               5                   10                  15

<210> SEQ ID NO 21
<211> LENGTH: 15
<212> TYPE: PRT
<213> ORGANISM: HIV

<400> SEQUENCE: 21

Ser Ile Leu Asp Ile Arg Gln Gly Pro Lys Glu Pro Phe Arg Asp
1               5                   10                  15

<210> SEQ ID NO 22
<211> LENGTH: 15
<212> TYPE: PRT
<213> ORGANISM: HIV

<400> SEQUENCE: 22

Ile Arg Gln Gly Pro Lys Glu Pro Phe Arg Asp Tyr Val Asp Arg
1               5                   10                  15

<210> SEQ ID NO 23
<211> LENGTH: 15
<212> TYPE: PRT
<213> ORGANISM: HIV

<400> SEQUENCE: 23

Pro Lys Glu Pro Phe Arg Asp Tyr Val Asp Arg Phe Tyr Lys Thr
1               5                   10                  15

<210> SEQ ID NO 24
<211> LENGTH: 15
<212> TYPE: PRT
<213> ORGANISM: HIV

<400> SEQUENCE: 24

Phe Arg Asp Tyr Val Asp Arg Phe Tyr Lys Thr Leu Arg Ala Glu
1               5                   10                  15

<210> SEQ ID NO 25
<211> LENGTH: 15
<212> TYPE: PRT
<213> ORGANISM: HIV

<400> SEQUENCE: 25

Val Asp Arg Phe Tyr Lys Thr Leu Arg Ala Glu Gln Ala Ser Gln
1               5                   10                  15

<210> SEQ ID NO 26
<211> LENGTH: 15
<212> TYPE: PRT
<213> ORGANISM: HIV

<400> SEQUENCE: 26

Tyr Lys Thr Leu Arg Ala Glu Gln Ala Ser Gln Glu Val Lys Asn
1               5                   10                  15

```
<210> SEQ ID NO 27
<211> LENGTH: 15
<212> TYPE: PRT
<213> ORGANISM: HIV

<400> SEQUENCE: 27

Arg Ala Glu Gln Ala Ser Gln Glu Val Lys Asn Trp Met Thr Glu
1               5                   10                  15

<210> SEQ ID NO 28
<211> LENGTH: 15
<212> TYPE: PRT
<213> ORGANISM: HIV

<400> SEQUENCE: 28

Ala Ser Gln Glu Val Lys Asn Trp Met Thr Glu Thr Leu Leu Val
1               5                   10                  15

<210> SEQ ID NO 29
<211> LENGTH: 15
<212> TYPE: PRT
<213> ORGANISM: HIV

<400> SEQUENCE: 29

Val Lys Asn Trp Met Thr Glu Thr Leu Leu Val Gln Asn Ala Asn
1               5                   10                  15

<210> SEQ ID NO 30
<211> LENGTH: 15
<212> TYPE: PRT
<213> ORGANISM: HIV

<400> SEQUENCE: 30

Met Thr Glu Thr Leu Leu Val Gln Asn Ala Asn Pro Asp Cys Lys
1               5                   10                  15

<210> SEQ ID NO 31
<211> LENGTH: 15
<212> TYPE: PRT
<213> ORGANISM: HIV

<400> SEQUENCE: 31

Leu Leu Val Gln Asn Ala Asn Pro Asp Cys Lys Thr Ile Leu Lys
1               5                   10                  15

<210> SEQ ID NO 32
<211> LENGTH: 15
<212> TYPE: PRT
<213> ORGANISM: HIV

<400> SEQUENCE: 32

Asn Ala Asn Pro Asp Cys Lys Thr Ile Leu Lys Ala Leu Gly Pro
1               5                   10                  15
```

BIORESORBABLE NONLAMELLAR MICROPARTICLES AND USES THEREOF

This is a Divisional of application Ser. No. 12/081,296 filed Apr. 14, 2008 and issued as U.S. Pat. No. 8,377,477 on Feb. 19, 2013, which is a Continuation of application Ser. No. 10/570,948 filed Mar. 7, 2006, which in turn is a U.S. National Phase of Application No. PCT/FR2004/050447, filed Sep. 21, 2004. The disclosure of the prior applications is hereby incorporated by reference herein in its entirety.

The present invention relates to novel bioresorbable particles to which protein substances are bonded, that are useful in particular in the field of vaccination.

Protein substances, such as proteins and peptides, also called antigens, are widely used in the treatment of many diseases, such as diseases of viral origin, generally in the form of a vaccine formulation.

In order to increase the activity and the strength of the antigen and to improve the stability of the pharmaceutical compositions containing the antigens, these compositions contain adjuvants. In this regard, vaccine formulations often comprise immunological adjuvants for enhancing cell-mediated responses and humoral responses.

Despite the presence of such adjuvants, conventional vaccines often have the drawback that they provide nonoriented protection against the pathogenic agents targeted. The term "oriented protection" is intended to mean protection involving both the cell-mediated response and the humoral response of the immune system.

In order to obtain an appropriate immune response, particulate carriers associated with antigens have been used, said antigens being either adsorbed onto the carrier, or trapped in the carrier. Such carriers possess multiple copies of the antigen of interest presented to the immune system and promote the trapping and retention of the antigens in the local lymph nodes. The particles can be phagocytozed by antigen-presenting cells and can increase antigen-presentation to the immune system. Examples of such carriers include poly(methyl methacrylate) polymers and also microparticles made of polylactides, such as poly(D- or L-lactic acid) known as D-PLA or L-PLA, respectively, and of poly(lactide-co-glycolide)s known as PLG.

PLG-based microparticles in which antigens are trapped are capable of giving an immune response. By way of example, Moore et al. (1995, Vaccine, 13:1741-1749) have shown that the microencapsulated HIV virus gp120 antigen induces an HIV-specific CD4+ and CD8+ T-cell response. Similarly, Vordemeier et al. (1995, Vaccine, 13-1576-1582) have shown that the PLG-trapped *Mycobacterium tuberculosis* antigen induces, in mice immunized with such an antigen, both a humoral response and a T-cell response.

Although these types of adjuvant offer some advantages compared with the other more toxic systems, they have the drawback that the production of microparticles is difficult and involves the use of corrosive chemical products, such as solvents, which can denature the antigen and destroy the immunogenicity thereof. Furthermore, the antigen may also be degraded due to the vigorous agitation required during the trapping process such as encapsulation.

It has thus been proposed to use microparticles which have the antigens adsorbed or grafted onto their surface (Rock K. L., Efficient MHC I presentation of exogenous Ag, PNAS 1993). Some authors, such as Eldrige et al., in Infect. Immun., 59:2978-2986 (1991), have, however, indicated that, in order to achieve an appropriate adjuvant effect, the antigens must be trapped in microparticles.

PCT patent application WO 97/02810 describes particles consisting of a biodegradable polymer, onto which antigens can be adsorbed. These particles are useful for the delivery of these antigens. The drawback of these particles is their lamellar nature due to the use of crystalline or partially crystalline polymers, such that it is not possible to control their size. In fact, particles intended for vaccination must have a submicronic size in order to be effective in transfection and in immunization.

Patent applications WO 98/33487 and WO 00/06123 describe, for their part, polylactide or PLG-based microparticles onto which antigens are adsorbed and the use thereof for stimulating immune responses. All the microparticles of these patent applications, onto which antigens are adsorbed, have been obtained using a surfactant in order to maintain the colloidal stability of said microparticles, and also a stabilizer, such as poly(vinyl alcohol), for the preparation of the polymer particles. The drawback of the microparticles thus obtained is their toxicity due to the presence in the microparticles of said surfactant and of said stabilizer.

The applicant has now discovered, against all expectations, that it is possible to obtain spherical, nonlamellar bioresorbable microparticles of at most micronic size, to which are bonded antigenic protein substances against which it is sought to trigger an immune response, and which are devoid of the above drawbacks, i.e. they are not toxic since they are prepared without stabilizer and without surfactant for the preparation of the polymeric microparticles, and without surfactant for the bonding of the antigens to the surface of the microparticles, without loss of colloidal stability.

Thus, a first subject of the invention consists of a method for preparing bioresorbable microparticles to which protein substances are bonded, characterized in that it comprises the steps of:
  (i) preparing said microparticles from at least one bioresorbable polymer without stabilizer and without surfactant, and
  (ii) bonding said protein substances to the microparticles obtained in step (i) without surfactant.

The microparticles obtained by means of the method of the invention are devoid of stabilizer and of surfactant such that they are novel.

Thus, another subject of the invention consists of the bioresorbable microparticles to which protein substances are bonded, which are obtainable by the method of the invention.

Against all expectations, the particles of the invention conserve their colloidal stability.

The microparticles of the invention are useful for stimulating both a cell-mediated response and a humoral response, such that they are useful both in therapy and in diagnosis.

Thus, another subject of the invention consists of the use of the microparticles of the invention for preparing a medicinal product, and also the pharmaceutical compositions, in particular vaccines, comprising the microparticles of the invention.

Finally, another subject of the invention consists of the use of the microparticles of the invention for the in vitro diagnosis of pathological states related to the protein substance bonded to said microparticles.

The microparticles intended for vaccination must not be toxic for the organism that receives them, while at the same time conserving their colloidal stability.

The method of the invention, that uses neither surfactant nor stabilizer, makes it possible, against all expectations, to obtain such particles.

The term "microparticle" is intended to mean particles of at most micronic, preferably at most submicronic, size so as to allow them to enter antigen-presenting cells.

The term "at most micronic size" is intended to mean a size of less than or equal to 999 μm, and the term "at most submicronic size" is intended to mean a size of less than or equal to 999 nm.

Preferably, the microparticles have a particle diameter of less than or equal to 3 μm. More preferably, the particles of the invention are of submicronic size, with preferably a diameter of between 150 and 900 nm, more preferably between 250 and 700 nm.

The size of the particles is readily determined by techniques known to those skilled in the art, such as, for example, using scanning electron microscopy, quasi-elastic light scattering or transmission electron microscopy.

The term "toxic microparticle" is intended to mean a microparticle comprising at least one compound capable of causing biological disorders, such as metabolic disturbances, in the organism having received the microparticle.

The first step of the method of the invention consists of the preparation of said microparticles from at least one bioresorbable polymer without stabilizer and without surfactant.

The term "bioresorbable polymer" is intended to mean a polymer capable of degrading, in the organism into which it has been introduced, into compounds that can be eliminated via the natural pathways. This polymer may be amorphous, slightly crystalline or crystalline.

Examples of such bioresorbable polymers include, without limitation, poly(α-hydroxylated acids), poly(hydroxybutyric acids), polycaprolactones, polyorthoesters and polyanhydrides. Preferably, the bioresorbable polymer used in the method of the invention is a poly(α-hydroxylated acid) such as poly(D-lactic acid), poly(L-lactic acid) (called PLA), poly(glycolic acid) (called PLG), or else a mixture of poly(α-hydroxylated acids), such as a mixture of poly(D- and L-lactic acids), a mixture of poly(L-lactic acid) and of poly(glycolic acid), a mixture of poly(D-lactic acid) and of poly(glycolic acid), or a mixture of poly(D-lactic and L-lactic acids) and of poly(glycolic acid), which constitutes an embodiment of the invention.

When the polymer used in the method of the invention is a mixture of poly(α-hydroxylated acids), the proportion of each constituent can be readily determined by those skilled in the art. Thus, for example, it is possible to use a racemic mixture of poly(D- and L-lactic acids) or a PLA/PLG mixture at various percentages known to those skilled in the art.

The preparation of the microparticles of the invention from at least one bioresorbable polymer can be carried out by any methods for preparing microparticles known to those skilled in the art, for which no stabilizer and no surfactant are used. In fact, step (i) of the method of the invention is characterized in that such agents are not used.

The stabilizers normally used in methods for preparing microparticles include, for example, poly(vinyl alcohol), pluronics (copolymer of poly(ethylene oxide) and of poly(propylene oxide)), and cationic or anionic surfactants such as cetyltrimethylammonium bromide or sodium dodecyl sulfate.

Of course, when the stabilizer used in the methods of the prior art is a surfactant, said methods do not use an additional surfactant.

The surfactants normally used in the methods of the prior art are largely known to those skilled in the art and are described, for example, in patent application WO 98/33487.

By way of example of a method for preparing microparticles without stabilizer and without surfactant, mention may be made of dialysis, solvent displacement, emulsification-solvent evaporation and emulsification-diffusion, these said methods being largely known to those skilled in the art.

For example, the dialysis for preparing the microparticles of the invention can be carried out with a solution of bioresorbable polymer in a water-miscible solvent, such as acetone, DMSO or DMF, at a concentration by mass of 0.1% to 10%, dialyzed against 1000 times its volume of water for 12 hours.

The second step of the method of the invention consists in bonding protein substances to the microparticles obtained in the first step of the method, without using surfactant.

This step of bonding the protein substance to the surface of the microparticles has the characteristic that it is carried out without surfactant. In fact, against all expectations, even in the absence of surfactant, the microparticles of the invention exhibit a colloidal stability that provides a range of particle size suitable for use in immunization.

By way of examples of a surfactant normally used for the bonding of protein substances to the surface of microparticles, reference may be made to the surfactants mentioned above.

The protein substances to be bonded to the surface of the microparticles obtained in step (i) of the method of the invention may be any protein substance against which it is sought to trigger an immune response.

The term "immune response" is intended to mean a cell-mediated response, a humoral response or both.

The term "cell-mediated response" is intended to mean a response mediated by T lymphocytes and/or other leukocytes. This response is reflected by the induction of a lytic activity by cytotoxic T lymphocytes and/or by cytokine production by suppressor CD8+T lymphocytes or by helper T cells.

The term "humoral response" is intended to mean a response mediated by the antibody molecules secreted by B lymphocytes.

The protein substances that are suitable for the purposes of the invention may be of several origins, such as of viral or bacterial origin.

By way of example of such protein substances, mention may, for example, be made of antigens and epitopes or any protein substance having the role of an antigen after bonding to the microparticles.

The antigens are molecules capable of being recognized by an antibody, the synthesis of which they have induced via an immune response, and containing at least one epitope. This may be whole proteins or protein fragments having conserved the structure of interest.

The epitopes are peptides comprising between 3 and 15 and generally between 5 and 15 amino acids, having also conserved the structure of interest.

According to a particular embodiment of the invention, the protein substance is an antigen of viral origin.

When the protein substance is of viral origin, the suitable viruses are any viruses for which substances capable of an immune response are known.

By way of example, mention may be made, without any limitation, of herpesviruses, hepatitis viruses, such as hepatitis B virus (HBV) and hepatitis C virus (HCV), papilloma viruses (HPV) and human immunodeficiency viruses (HIV), such as HIV-1 and HIV-2.

The nucleic acid sequences of the viruses suitable for the purposes of the invention, and also the proteins encoded by said sequences, are largely known to those skilled in the art and are available, for example, in databases such as GenBank.

Thus, for example, the HIV virus has genes which encode structural proteins of the virus. The gag gene encodes the protein that forms the core of the virion, including the p24 antigen. The poi gene encodes the enzymes responsible for reverse transcription (reverse transcriptase), for cleavage (protease) and for integration (integrase). The env gene encodes the envelope glycoproteins. It contains six other genes (tat, rev, nef, vif, vpr and vpu (HIV-1) or vpx (HIV-2)) which encode proteins involved in regulating the expression of the genes of the virus (regulatory proteins). The HIV genome also comprises the 5' and 3' LTRs (Long Terminal Repeats) which comprise regulatory elements involved in the expression of the genes of the virus.

According to one embodiment of the invention, the protein substance used in the method of the invention is an HIV virus antigen. Preferably, the HIV virus antigen is a regulatory protein or the p24 protein, the preferred regulatory proteins being the Tat, Rev or Nef protein.

As regards HCV, the 5' end of its genome corresponds to an untranslated region adjacent to the genes which encode the structural proteins, the nucleocapsid core protein, the two envelope glycoproteins, E1 and E2, and a small protein called p7. The 5' untranslated region and the core gene are relatively well conserved in the various genotypes. The E1 and E2 envelope proteins are encoded by regions that are more variable from one isolate to another. The p7 protein is an extremely hydrophobic protein which is thought to constitute an ion channel. The 3' end of the HCV genome contains the genes which encode the nonstructural proteins (NS2, NS3, NS4, NS5) and a 3' noncoding region that has a well-conserved domain (Major M E, Feinstone S M, Hepatology, June 1997, 25(6):1527-1538).

The NS3 nonstructural protein of HCV is a 630 amino acid protein which comprises two distinct structural domains: an N-terminal domain, of 81 amino acids, which has an active serine protease activity involved in the maturation of the viral protein (domain called NS3 protease), and a C-terminal domain, of 549 amino acids, comprising a helicase activity associated with an NTPase activity which plays a role in the replication of the viral genome (domain called NS3 helicase). This NS3 protein is relatively well-conserved among the various genotypes of the virus, such that this protein constitutes a "vaccine candidate" antigen of choice.

According to one embodiment of the invention, the protein substance of interest is an antigenic protein of HCV, preferably a nonstructural protein, more preferably the NS3 protein, and in particular the NS3 helicase protein being more preferred.

The protein substances suitable for the purposes of the invention can be obtained by the genetic engineering technique which comprises the steps of:
  culturing a microorganism or eukaryotic cells transformed with a nucleotide sequence encoding the protein substance of interest, and
  recovering said protein substance produced by said microorganism or said eukaryotic cells.

This technique is well known to those skilled in the art. For further detail with regard thereto, reference may be made to the manual hereinafter: Recombinant DNA Technology I, Editors Ales Prokop, Raskesh K Bajpai; Annals of the New-York Academy of Sciences, Volume 646, 1991.

The protein substances of interest, when they are small in size, can also be prepared by conventional peptide syntheses well known to those skilled in the art.

The bonding of the protein substances to the bioresorbable microparticles can be carried out by any method known to those skilled in the art.

Examples of such bonding include adsorption, covalent bonding and bonding via a polysaccharide polymer deposited at the surface of the microparticle, such as chitosan, the protein substance being bonded to the chitosan by adsorption.

The adsorption can be carried out, for example, by mixing the microparticles with the protein substances and incubating with agitation, for example at ambient temperature or at 37° C.

The covalent bonding of the protein substances to the surface of the microparticles can be carried out using the techniques and reagents known in the literature, as described, for example, in Bioconjugate Techniques, G. T. Hermanson, Academic Press, London, 1996 and Chemical Reagents for Protein Modification, R. L. Lundblad, Ed. CRC Press, 1991.

According to a particular embodiment, the bonding of the protein substances to the microparticles is carried by adsorption.

The bioresorbable microparticles to which protein substances are bonded, prepared according to the method of the invention, are devoid of stabilizer and of surfactant, such that they are novel and constitute another subject of the invention.

The microparticles of the invention, because of their ability to induce an immune response by virtue of the protein substance, and because of their lack of toxicity, are particularly suitable for the preparation of pharmaceutical compositions, in particular vaccines, that are useful in the treatment of pathologies associated with the protein substance bonded to the microparticles.

Thus, another subject of the invention consists of the use of the bioresorbable microparticles of the invention, for preparing a medicinal product.

In particular, the medicinal product prepared with the microparticles of the invention is particularly useful for the inhibition, prevention or treatment of an infection caused by a virus, such as, for example, the HIV or HCV virus or any other known virus, which constitutes another embodiment of the invention.

The invention also relates to a pharmaceutical composition, in particular a vaccine, containing at least one microparticle of the invention and, where appropriate, a pharmaceutically acceptable excipient.

The pharmaceutical compositions of the invention are suitable for oral, sublingual, subcutaneous, intramuscular, intravenous, topical, local, intratracheal, intranasal, transdermal, rectal, intraocular or intra-auricular administration, it being possible for said active ingredient to be administered in unit administration forms.

The unit administration forms may, for example, be tablets, gelatin capsules, granules, powders, injectable oral solutions or suspensions, transdermal patches, sublingual, buccal, intratracheal, intraocular, intranasal or intra-auricular administration forms, forms of administration by inhalation, topical, transdermal, subcutaneous, intramuscular or intravenous administration forms, rectal administration forms, or implants. For topical administration, creams, gels, ointments, lotions or eye lotions can be envisioned.

These pharmaceutical forms are prepared according to the usual methods in the fields under consideration.

Of course, those skilled in the art will readily determine the suitable excipient and the amount of microparticles to be used according to the constituents and to the unit administration form of the pharmaceutical composition.

Said unit forms contain a dosage so as to allow daily administration of from 0.001 to 10 mg of active ingredient per kg of body weight, according to the pharmaceutical form.

There may be specific cases where higher or lower dosages are appropriate; such dosages do not depart from the scope of the invention. According to the usual practice, the dosage appropriate for each patient is determined by the physician according to the method of administration and the weight and response of the patient.

According to another embodiment of the invention, the present invention also relates to a method of treating pathologies associated with the protein substance bonded to the microparticle of the invention, which comprises the administration, to a patient, of an effective dose of a pharmaceutical composition of the invention.

The microparticles of the invention also make it possible to obtain antibodies, which constitutes another subject of the invention.

The antibodies according to the invention are polyclonal or monoclonal antibodies, monoclonal antibodies being preferred.

The abovementioned polyclonal antibodies can be obtained by immunization of an animal with at least one microparticle of the invention, followed by recovery of the desired antibodies in purified form, by taking a sample of the serum of said animal and separating said antibodies from the other constituents of the serum, in particular by affinity chromatography on a column to which is attached an antigen specifically recognized by the antibodies, in particular that of the microparticle of the invention.

The monoclonal antibodies can be obtained by means of the hybridoma technique, the general principle of which is recalled hereinafter.

Firstly, an animal, generally a mouse (or cells in culture in the case of in vitro immunizations), is immunized with at least one microparticle of the invention, for which the B lymphocytes are then capable of producing antibodies against the protein substance of said microparticle. These antibody-producing lymphocytes are then fused with "immortal" (murine in the example) myeloma cells so as to give hybridomas. Using the heterogeneous mixture of the cells thus obtained, a selection of the cells capable of producing a specific antibody and of indefinitely multiplying is then carried out. Each hybridoma is multiplied in the form of a clone, each resulting in the production of a monoclonal antibody whose recognition properties with respect to the microparticle of the invention may be tested, for example, by ELISA, by one- or two-dimensional immunoblotting, by immunofluorescence, or using a biosensor. The monoclonal antibodies thus selected are subsequently purified, in particular according to the affinity chromatography technique described above.

The microparticles and the antibodies of the invention are also useful in the diagnosis of the pathological state associated with the protein substance bonded to the surface of said microparticles.

Specifically, the microparticles or antibodies of the invention can be used as a partner for the capture or detection of an analyte in any diagnostic technique using such partners, such as the ELISA method. For example, when the intention is to search for an antigen as an analyte, an antibody of the invention obtained from microparticles to which said antigen is bonded is used, whereas, if the intention is to search for antibodies, the microparticles of the invention are used. In the latter case, if the diagnostic test requires the use of a solid support, the microparticles may or may not play this role.

Thus, another subject of the invention consists of a diagnostic composition consisting of the bioresorbable microparticles or of the antibodies of the invention.

It also relates to the use of this diagnostic composition for the in vitro diagnosis of the pathological state related to the protein substance bonded to the bioresorbable microparticle, it being possible for the pathological state to be, according to one embodiment, a viral infection, as caused by the HIV virus or the HCV virus.

Here again, those skilled in the art will readily determine the amount of microparticles or antibodies to be used according to the diagnostic technique used.

Figure 3:
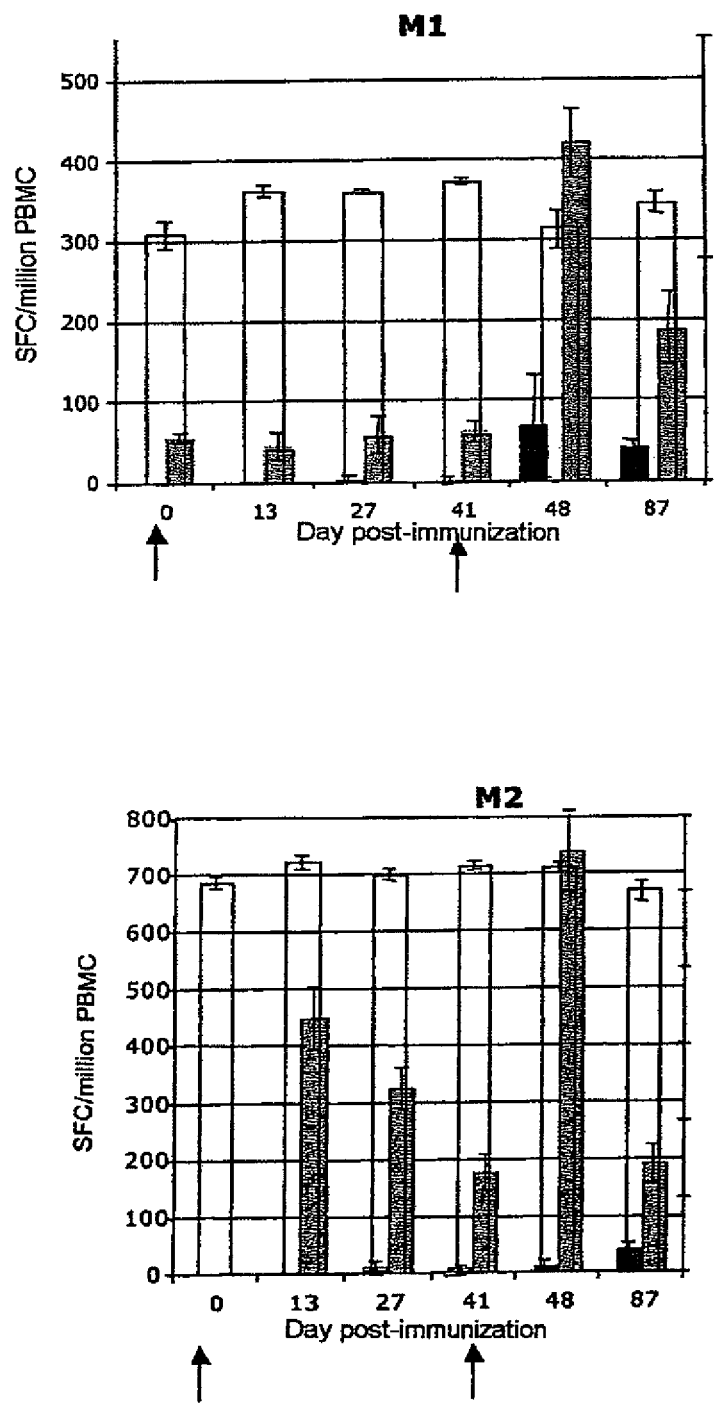
Figure 4:
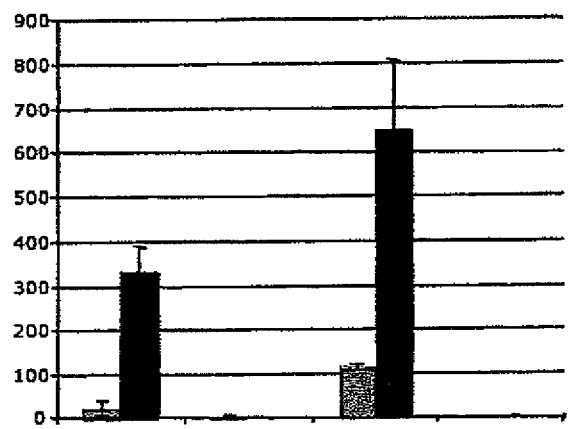
Figure 4:
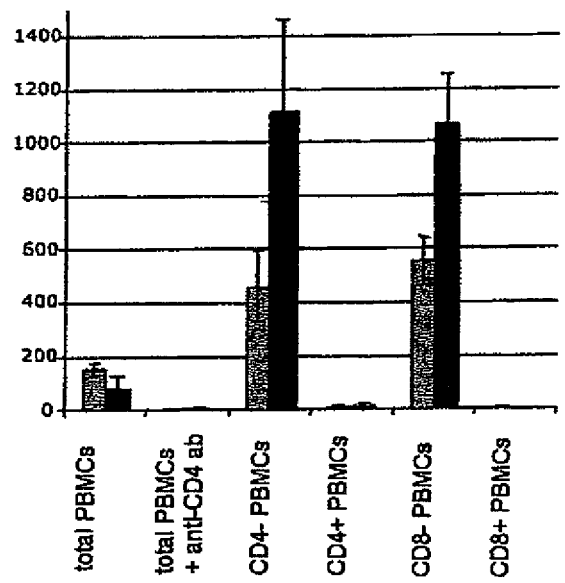
Figure 5:
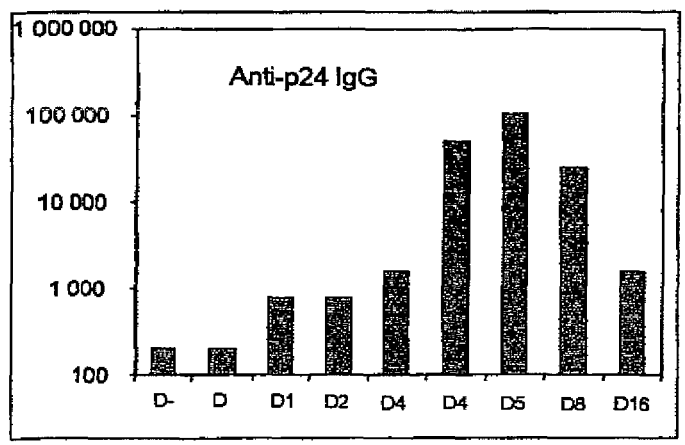
Figure 6:
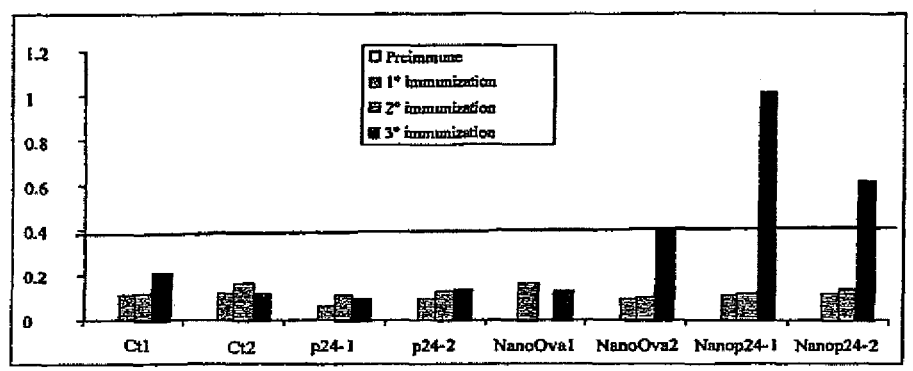
Figure 7:
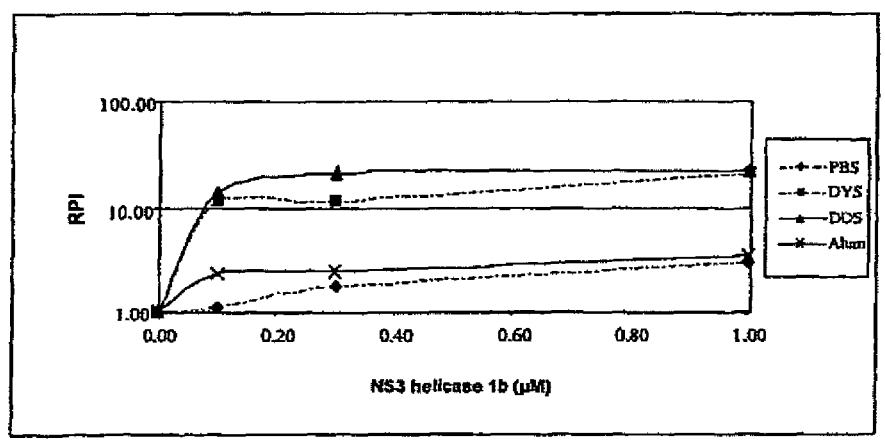
Figure 8A:
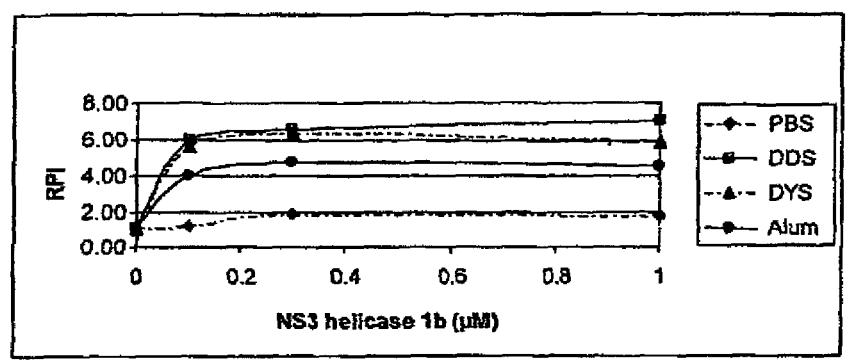
Figure 8B:
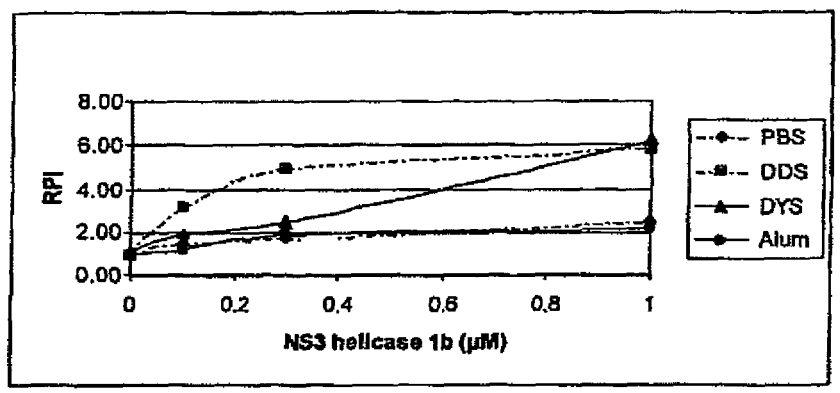
Figure 9:
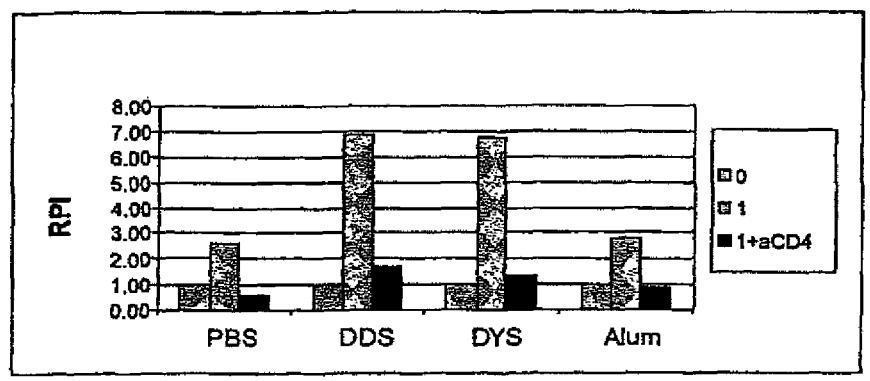

The present invention will be understood more fully from the following examples given only by way of nonlimiting illustration, and also from FIGS. 1 to 9, in which:

FIG. 1 gives the result of CTL assays by immunizing mice with the DNA sequence corresponding to the HCV NS3NS4 polyprotein as a control (FIG. 1A), with the NS3 helicase protein substance and Freund's adjuvant, without microparticle (FIG. 1B), with the NS3 helicase protein substance without microparticle (FIG. 1C), with PLA microparticles without protein substance (FIG. 1D), and with the microparticles of the invention in which the polymer is PLA and the protein substance is the NS3 helicase peptide (FIG. 1E), FIG. 2 represents a histogram giving the anti-p24 IgG titers according to an ELISA assay, in the preimmune sera and the immune sera of six rabbits (L1 to L6) having been given an injection of the particles of the invention PLA-p24 either intradermally (ID) or subcutaneously (SC), FIG. 3 represents histograms (mean of four replicates +/−standard deviations) obtained according to an ELISPOT assay in two macaques M1 and M2 having received microparticles of the invention PLA/p24, giving the number of spots per million cells obtained as a function of the days post-immunization after stimulation without antigen (medium, negative control, black histogram), after stimulation with p24 (gray histogram) or after stimulation with the PMA-ionomycin couple (outline histogram), FIG. 4 represents histograms giving the number of spots obtained by ELISPOT in two macaques M1 and M2 having received microparticles of the invention PLA/p24, after stimulation either with the p24 protein (black histogram), or with the peptides (gray histogram), in the total PBMC fraction, the total PBMC fraction in the presence of the anti-CD4 antibody, the CD4$^+$-depleted PBMC fraction (CD4− PBMC) and the corresponding CD4$^+$-enriched fraction (CD4+ PBMC), and also the CD8$^+$-depleted PBMC fraction (CD8− PBMC) and the corresponding CD8$^+$-enriched fraction (CD8+ PBMC), FIG. 5 represents histograms giving the anti-p24 IgG titer obtained by ELISA in the M2 monkey having received microparticles of the invention PLA/p24, as a function of the days on which the sequential sera were taken, FIG. 6 represents histograms giving the OD value obtained by ELISA in the preimmune serum, in the serum after the 1st immunization, in the serum after the second immunization and in the serum after the 3rd immunization of mice immunized with SRDC cells and sensitized either with the negative control (Ct1 and Ct2), or with the p24 protein (p24-1 and p24-2), or with the microparticles negative control (NanoOval and NanoOva2) or with the microparticles of the invention (Nanop24-1 and Nanop24-2), FIG. 7 represents graphs giving the relative proliferative index (RPI) specific to the NS3h protein as a function of the amount of NS3h used in mice having received NS3h-PBS (PBS), of the microparticles of the invention prepared by dialysis (DYS), of the microparticles of the invention prepared by solvent displacement (DDS) and the NS3h-Alum composition, FIG. 8 represents graphs giving the relative proliferative index (RPI) specific to the NS3h protein as a function of the amount of NS3h used in mice having received NS3h-PBS (PBS), of the microparticles of the invention prepared by dialysis (DYS), of the microparticles of the invention prepared by solvent displacement (DDS) and the NS3h-Alum composition (Alum) in the cells of the popliteal nodes for the localized cellular response (FIG. 8A) and in the cells of the spleen for the systemic cellular response (FIG. 8B), and FIG. 9 represents histograms giving the cellular proliferative index (RPI) as a function of the immunogens used in mice, i.e. NS3h-PBS (PBS), of the microparticles of the invention prepared by dialysis (DYS), of the microparticles of the invention prepared by solvent displacement (DDS) and the NS3h-Alu composition (Alum), in the cells of the spleen without stimulation (0), after stimulation with NS3h protein (1) or after stimulation with protein and the anti-CD4$^+$ antibody (1+aCD4).

EXAMPLE 1: PREPARATION OF MICROPARTICLES OF THE INVENTION BY Dialysis

1. Preparation of PLA Particles

PLA 50 (50% of poly(L-lactic acid) and 50% of poly(D-lactic acid)) of molar mass 52 000 Da (PHUSIS®) was used.

This PLA was dissolved at 2% by total weight of solution in DMSO (PROLABO®). The organic solution of PLA was subsequently introduced into a dialysis membrane with a cut off of 15 000 Da (SPECTRUM®) and the assembly was placed in a water bath of double-distilled water (4 l, MILLIQ®), stirred and changed regularly every hour, for 6 h. The final dialysis bath was continued overnight in order to obtain particles as a precipitate.

The following day, the solution of PLA particles was recovered and stored at 4° C.

The particles thus obtained were characterized in terms of their size, their polydispersity index and their charge using the Zetasizer 3000 HS device (MALVERN® INSTRUMENTS). Their solids content was also evaluated after weighing, by means of the calculation: (mass of dry extract/mass of wet extract)×100.

2. Preparation of PLA/p24 Particles

The HIV-1 p24 protein was prepared in recombinant form in *E. coli* and was purified by metal-chelate affinity chromatography according to the technique of Cheynet V., et al., 1993, Protein Expr. Purif., 4:367-372.

The PLA microparticles were prepared as described in point 1 above and have a particle diameter of 515.7+/−6.7 nm, a solids content of 1.1% and a polydispersity index of 0.242+/−0.013.

A 10 mM phosphate buffer, pH 5.7, was prepared by mixing 10 ml of 0.1M phosphate buffer, pH 4.7 (NaH$_2$PO$_4$.2H$_2$O, M=15.60 g/l) and 1.1 ml of 0.1M phosphate buffer, pH 9.2 (NaH$_2$PO$_4$.2H$_2$O, M=17.79 g/l), and diluting to 1/10th with water.

200 μl of the p24 protein diluted to 0.6 g/l in the 10 mM phosphate buffer, pH 5.7 were mixed with 200 μl of the microparticles, and stirring was carried out overnight on a wheel at ambient temperature. Centrifugation was then carried out for 5 min at 5000 rpm and the supernatant was drained, which made it possible to assay the amount of nonadsorbed p24 (BCA Protein Assay kit from Pierce) and to deduce therefrom the concentration of p24 adsorbed onto the microparticles, which comes to 0.2 g/l.

3. Preparation of the PLA/Tat Microparticles

The HIV-1 Tat protein, of SEQ ID NO: 1, synthesized according to the procedure described in Péloponèse J. P., et al., 1999, The Journal of Biological Chemistry, 274(17): 11473-11478, was used.

The PLA microparticles were prepared as described in point 1 above and have a particle diameter of 420.1+/−10.7 nm, a solids content of 1.02% and a polydispersity index of 0.241+/−0.040.

200 μl of the Tat protein diluted to 0.4 g/l in a degassed 10 mM phosphate buffer, pH 6.8, prepared as indicated in point 2 above, except that 13.8 ml of 0.1M phosphate buffer, pH 9.2, were used, were mixed with 200 μl of the microparticles, and stirring was carried out overnight on a wheel at ambient temperature. Centrifugation was then carried out for 5 min at 5000 rpm and the supernatant was drained, which made it possible to assay the amount of nonadsorbed Tat (BCA Protein Assay kit from Pierce) and to deduce therefrom the concentration of Tat adsorbed onto the microparticles, which comes to 0.1 g/l.

4. Preparation of the PLA/NS3 Helicase Microparticles

The HCV NS3 helicase peptide of SEQ ID NO: 2 obtained in recombinant form as follows, was used.

The gene encoding amino acids 1192-1458 corresponding to the helicase domain of the HCV NS3 protein as a fusion with hexahistidine was cloned into the prokaryotic expression vector pMH80 and expressed in *E. coli* JM109 bacteria (Promega). The expression of the recombinant protein was carried out at 30° C. after 3 hours of induction with 1 mM IPTG (isopropyl-beta-D-thiogalactopyranoside, Promega). After centrifugation, the bacteria were lysed by sonication in the buffer solution: 10 mM Tris-HCl, pH 8, 5 mM MgCl$_2$, 1% Triton X100, 1 tablet of anti-protease (Boehringer), 250U benzonase (Merck). After lysis and centrifugation, the soluble fraction was purified on a Ni-agarose column and eluted in 10 mM sodium phosphate buffer solution, pH 7.2, containing 300 mM NaCl and 300 mM imidazole. The pure protein was thus dialyzed against PBS, pH 7.2. After purification, the protein was analyzed by acrylamide gel electrophoresis in the presence of sodium dodecyl sulfate (SDS), and mass spectrometry. The degree of purity of the NS3 protein, helicase domain, is estimated at greater than 95%. The absence of endotoxin was verified by measuring the degree of endotoxins (LPS) with an in vitro LAL and functional assay.

The PLA microparticles were prepared as described in point 1 above and have a particle diameter of the order of 600 nm, a solids content of 1% and a polydispersity index of 0.2.

200 μl of the NS3 helicase peptide diluted to 0.327 g/l in a 10 mM phosphate buffer, pH 6.5, prepared as described in point 2 above, except that 6.8 ml of 0.1M phosphate buffer, pH 9.2, were used, were mixed with 200 μl of the microparticles, and stirring was carried out overnight on a wheel at ambient temperature. Centrifugation was then carried out for 5 min at 5000 rpm and the supernatant was drained, which made it possible to assay the amount of nonadsorbed NS3 helicase (BCA Protein Assay kit from Pierce) and to deduce therefrom the concentration of NS3 helicase adsorbed onto the microparticles, which comes to 0.28 g/l.

EXAMPLE 2: PREPARATION OF MICROPARTICLES OF THE INVENTION BY SOLVENT DISPLACEMENT

1. Preparation of PLA Particles

PLA 50 (50% of poly(L-lactic acid) and 50% of poly(D-lactic acid)) of molar mass 52 000 Da (PHUSIS®) was used.

This PLA was dissolved at 2% by a total weight of solution in acetone. The solution of PLA in acetone was then added, dropwise, to 35 ml of water and the solvent was evaporated off under reduced pressure for 35 min.

The particles thus obtained were characterized in terms of their size, their polydispersity index and their charge using the Zetasizer 3000 HS device (MALVERN® INSTRUMENTS). Their solids content was also evaluated after weighing, by means of the calculation: (mass of dry extract/mass of wet extract)×100.

2. Preparation of the PLA/NS3 Helicase Microparticles

The HCV NS3 helicase peptide of SEQ ID NO: 2 obtained in recombinant form as indicated in example 1, point 4 above was used.

The PLA microparticles were prepared as described in point 1 above and have a particle diameter of the order of 250 nm, a solids content of 1% and a polydispersity index of 0.3.

200 μl of the NS3 helicase peptide diluted to 0.327 g/l in a PBS buffer (Phosphate Buffered Saline buffer; 150 mM NaCl, pH 7.1), prepared as described in point 1 above, except that 6.8 ml of 0.1M PBS buffer, pH 9.2, were used, were mixed with 200 μl of the microparticles, and stirring was carried out overnight on a wheel at ambient temperature. Centrifugation was then carried out for 5 min at 5000 rpm and the supernatant was drained, which made it possible to assay the amount of nonadsorbed NS3 helicase (BCA Protein Assay kit from Pierce) and to deduce therefrom the concentration of NS3 helicase adsorbed onto the microparticles, which comes to 0.34 g/l.

EXAMPLE 3: IMMUNIZATION OF MICE WITH THE PLA/P24 MICROPARTICLES OF THE INVENTION

1. Animal Model

The immunization experiments were carried out on female BALB/c ($H-2^d$) mice 6 to 8 weeks old at the time of the first immunization.

2. Immunogens Administered

In this experiment, the p24 protein alone, the PLA/p24 microparticles of the invention prepared as indicated in example 1, point 2 above, and also the p24-Freund's adjuvant (Sigma) composition prepared in the form of a water-in-oil emulsion, and which is known to exhibit a good immunogenic capacity (positive control), were used.

3. Immunizations

The mice received three successive doses (40 μg or 10 μg each) of the immunogens described in point 2 above at 0, 2 and 4 weeks. All the injections were given subcutaneously.

The animals were sacrificed 10 days (D38), 14 days (D42) or else 42 days (D70) after the third injection and the blood and the spleen were taken for the immunological analyses.

4. Immunological Analyses

The humoral response and the cellular response were investigated as follows:

Humoral response: a blood sample was taken from the mice before they were sacrificed. The presence of anti-p24 antibodies (IgG1, IgG2a and IgG) was determined by ELISA. The p24 protein was used for capture and the specific antibodies present in the serum were revealed with anti-mouse polyclonal antibodies as detection antibodies, which antibodies bind to the antibodies being sought and are, respectively, a horseradish peroxidase-labeled goat anti-mouse IgG1 antibody (Southern Biotechnology Associates Inc., Cat no. 1070-05, Birmingham, Ala., USA), a horseradish peroxidase-labeled goat anti-mouse IgG2a antibody (Southern Biotechnology Associates Inc., Cat no. 1080-05), and a horseradish peroxidase-conjugated AffiniPure goat anti-mouse IgG antibody (H+L, Jackson Immunoresearch, Cat no. 115-035-062). The titer is the inverse of the dilution for which an absorbance of 0.3 OD unit is obtained with the ELISA protocol used. The ratio of the IgG2a:IgG1 isotypes, which makes it possible to judge the IFN-γ-IL-4 tendency (respectively, Th1-Th2) of the immune response, was also determined by indirect ELISA.

Cellular response: after sacrifice of the mice, the spleens were removed sterilely so as to prepare a cell suspension. The following analyses were carried out on the cell suspensions obtained, each mouse having been analyzed individually.

(i) CTL Assay:

The cell suspension was placed in culture in the presence of a 9-mer peptide (AMQMLKETI, SEQ ID NO: 3) which corresponds to an immunodominant $H-2K^d$-restricted CTL epitope, and of IL-2. Five days later, the effector population was restimulated with irradiated naïve cells loaded with the peptide. The effector cytotoxic population was harvested after the 7th day and the CTL activity was measured using $^{51}$Cr-labeled P815 cells as targets.

(ii) ELISPOT:

The ELISPOT makes it possible to determine the number of cells secreting a given cytokine in response to a specific stimulus. We were interested in the cytokine IFN-γ (Th1). The cell suspensions obtained from the spleens were restimulated in vitro with the peptide (AMQMLKETI, SEQ ID NO: 3) for 20 h in order to analyze the CD8-type responses.

96-well ELISPOT plates with PVDF membranes (Multiscreen IP, Millipore) were coated with an anti-IFN-γ antibody. During the restimulation, the splenocyte suspensions were incubated in these plates so as to capture the cytokines secreted by each cell. The spots corresponding to each cell secreting the cytokine of interest were visualized with a biotinylated detection antibody specific for the cytokine of interest.

(iii) Proliferation: The splenocytes were stimulated in the presence of the p24 protein for 5 days. The cells were pulsed for 18 h with tritiated thymidine, which incorporates into the DNA of the cells undergoing proliferation. Following the pulse, the cells were harvested on a membrane which retains the DNA and makes it possible to eliminate the nonincorporated labeled thymidine by washing. The more the cells proliferate in response to the specific stimulus, the more the DNA is labeled; in other words, the greater the cellular response against the immunogen (p24).

5. Results

A first series of experiments was carried out with 15 mice (5 mice per branch), three doses of 10 μg of immunogen and sacrifice of the mice at D38, and investigation of the humoral response and the CTL assay and proliferation as cellular response.

The results are given in table 1 below:

TABLE 1

|  | p24 alone | p24/Freund's | p24/PLA |
|---|---|---|---|
| Proliferation (Δcpm)[a] | 3000 | 3900 | 8000 |
| CTL[b] | 0/5 | 0/5 | 0/5 |
| IgG1 antibodies (titer)[c] | $0.1 \times 10^5$ | $10 \times 10^5$ | $7 \times 10^5$ |

[a]Mean of the cpm values (specific stimulation − stimulation with medium), cpm = counts per minute (Student's test, P = 0.002)
[b]Number of mice having specific CTL activity out of the total number of mice of the branch
[c]Geometric mean of the anti-p24 IgG1 titers of the mice of the branch This table demonstrates that:
enhanced proliferative responses are obtained with the p24/PLA microparticles of the invention, compared with the p24 protein alone or adjuvanted with Freund's,
no CTL activity is detected with any one of the immunogens, and
the p24/PLA microparticles of the invention make it possible to obtain a specific antibody titer that is largely superior to that obtained when p24 alone is administered, the responses obtained being within the order of magnitude of the antibody titers obtained with the p24/Freund's adjuvant combination.

The experiment was repeated with 13 mice (3 or 4 mice per branch), except that the immunogens were used at a rate of 40 µg and that the mice were sacrificed either at D42 (3 mice) or at D70 (4 mice).

The results are given in table 2 below.

TABLE 2

|  | p24 alone | p24/Freund's | p24/PLA D 42 | p24/PLA D 70 |
|---|---|---|---|---|
| ELISPOT IFN-γ CD8[a] | 6 | 100 | 50 | 330 |
| CTL[b] | 0/3 | 0/3 | 0/3 | 4/4 |
| IgG1 antibodies (titer)[c] | $0.7 \times 10^5$ | $10 \times 10^5$ | $8 \times 10^5$ | $30 \times 10^5$ |

[a]Mean of the number of cells secreting IFN-γ/10[6] total cells, in response to a specific stimulus (peptide AMQMLKETI, SEQ ID NO: 3) for 20 h
[b]Number of mice having specific CTL activity out of the total number of mice of the branch
[c]Geometric mean of the anti-p24 IgG1 titers of the mice of the branch The results in the table demonstrate that:
if the antibody titers reported in table 1 are compared with those reported here in table 2, increasing the dose from 10 µg to 40 µg makes it possible to give comparable results, and
a more long-term response after the final injection, reflected by a later sacrifice of the mice, makes it possible to demonstrate a CTL response in all the mice of the p24/PLA group, and also a response by ELISPOT and in terms of enhanced antibody titers.

EXAMPLE 4: IMMUNIZATION OF MICE WITH THE PLA/TAT MICROPARTICLES OF THE INVENTION

The procedure indicated in example 3 was repeated, except that the PLA/Tat microparticles as prepared in example 1, point 3 above, the Tat protein alone and the Tat protein/Freund's adjuvant (Sigma) combination prepared in the form of a water-in-oil emulsion were used as immunogen, that the injection doses were each 20 µg, that, for the humoral response, the Tat protein was used as capture partner and the mouse polyclonal antibodies as indicated in example 3, point 4 above were used as detection partner, and that, for the humoral response, only an ELISPOT assay was carried out, using as stimulus either the six peptides as indicated hereinafter, for 20 h, for analyzing the CD8-type responses, or the Tat protein, for 42 h, for analyzing the CD4-type responses.

Peptides Used in the ELISPOT Assay (Sygma Genosys)

CFHCQVCFTKKGLGI (SEQ ID No. 4)

VCFTKKGLGISYGRK (SEQ ID No. 5)

KGLGISYGRKKRRQR (SEQ ID No. 6)

SYGRKKRRQRRRSPQ (SEQ ID No. 7)

KRRQRRRSPQDSETH (SEQ ID No. 8)

RRSPQDSETHQVSLS (SEQ ID No. 9)

The results are indicated in table 3 below.

TABLE 3

|  | Tat alone | Tat/Freund's | Tat/PLA |
|---|---|---|---|
| ELISPOT IFN-γ CD8[a] | 3 | 3 | 24 |
| ELISPOT IFN-γ CD4[b] | 4 and 6 | 4 and 8 | 28 and 50 |
| IgG antibodies (titer)[c] | $0.1 \times 10^5$ | $0.2 \times 10^5$ | $1.7 \times 10^5$ |
| IgG2a antibodies (frequency)[d] | 2/4 | 1/4 | 3/4 |
| IgG2a antibodies (titer)[e] | 730 | 560 | 3900 |

[a]Mean of the number of cells secreting IFN-γ/10[6] total cells, in response to a specific stimulus (pool of peptides) for 20 h
[b]Mean of the number of cells secreting IFN-γ/10[6] total cells, in response to a specific stimulus (Tat protein) for 42 h
[c]Geometric mean of the anti-Tat total IgG titers of the mice of the branch
[d]Number of mice having a specific IgG2a response out of the total number of mice of the branch
[e]Geometric mean of the anti-Tat IgG2a titers of the mice which have responded The results in table 3 above demonstrate that:
injection of the microparticles of the invention makes it possible to induce IFN-γ-secreting cells, whereas injection of the Tat protein alone or of the Tat/Freund's composition, and
bonding of the Tat protein to the PLAs makes it possible to enhance the antibody titers (total IgGs) by approximately 1 log compared with the titers obtained with the Tat protein alone or adjuvanted with Freund's, which are of the order of $10^4$. The use of the Tat/PLA microparticles makes it possible to enhance both the frequency and the titer of the anti-Tat IgG2as.

EXAMPLE 5: IMMUNIZATION OF MICE WITH THE PLA/NS3 HELICASE MICROPARTICLES OF THE INVENTION

1. Animal Model

The immunization experiments were carried out on 14 C57BL/6 mice transgenic for the HLA-A2 molecule (Pascolo S., et al. (1997), J. Exp Med., 185(12), 2043-2051).

2. Immunogens Administered

In this experiment, naked DNA corresponding to the NS3NS4 nucleic acid sequence (SEQ ID NO: 10) as a positive control, the NS3 helicase peptide alone, the PLA particles alone, as prepared in example 1, points 1 and 4 above, the NS3 helicase/Freund's adjuvant (Sigma) composition prepared in the form of a water-in-oil emulsion and also the PLA/NS3 helicase microparticles of the invention as prepared in example 1, point 4 above, were used.

3. Immunizations

The mice received three successive doses of the immunogens described in point 2 above, at 0, 2 and 4 weeks, at a rate of 50 µg each in the case of the proteins or of 100 µg each in the case of the naked DNA. All the injections were given subcutaneously, with the exception of the naked DNA, which was administered intramuscularly.

The animals were sacrificed approximately 70 days (D70) after the first injection and the blood and the spleen were taken for the immunological analyses.

4. Immunological Analyses

The CTL cellular response was investigated as follows: after sacrifice of the mice, the spleens were removed sterilely in order to prepare a cell suspension. The cell suspension was placed in culture in the presence of the KLV peptide (KLVALGVNAV, SEQ ID NO: 11), which corresponds to a CTL epitope contained in the NS3 protein, and of IL-2. Five days later, the effector population was restimulated with irradiated naïve cells loaded with the peptide. The effector cytotoxic population was harvested after the 7th day and the CTL activity was measured using $^{51}$Cr-labeled P815 cells as targets.

5. Results

The results are given in FIG. 1, representing graphs giving the percentage specific lysis as a function of the effector/target ratio, and where FIG. 1A gives the cellular response induced after injection of the DNA sequence corresponding to the HCV NS3NS4 polyprotein as a control, FIG. 1B gives the cellular response induced after injection of the NS3 helicase/Freund's adjuvant combination without microparticle, FIG. 1C gives the cellular response induced after injection of the NS3 helicase peptide without microparticle, FIG. 1D gives the cellular response induced after injection of the PLA microparticles without protein substance, and FIG. 1E gives the cellular response induced after injection of the PLA/NS3 helicase microparticles of the invention.

These graphs show a CTL response specific for the NS3 helicase peptide, demonstrated when the PLA/NS3 microparticles of the invention are injected.

EXAMPLE 6: IMMUNIZATION OF RABBITS WITH THE PLA/P24 MICROPARTICLES OF THE INVENTION

1. Animal Model

The immunization experiments were carried out on New Zealand White strain rabbits weighing approximately 2.5 kg at the time of the first immunization.

2. Immunogens Administered

In this experiment, the PLA/p24 microparticles of the invention prepared as indicated in example 1, point 2 above, and also the p24-Freund's adjuvant (Sigma) composition prepared in the form of a water-in-oil emulsion, and which is known to exhibit a good immunogenic capacity (positive control), were used.

3. Immunizations

The rabbits received five successive doses of 200 µg of the immunogens described in point 2 above at 0, 1, 2, 3 and 4 months. All the injections were given subcutaneously or intradermally.

4. Monitoring of the Appearance of the Anti-p24 Humoral Response

In order to follow the appearance of the anti-p24 antibodies, blood samples were taken regularly from the animals. The presence of the anti-p24 antibodies was then tested using the ELISA assay similar to that described in example 3, point 4, except that the visualizing conjugate was replaced with a horseradish peroxidase-conjugated AFFINIPURE goat anti-rabbit IgG antibody (H+L, Jackson Immunoresearch, Cat no. 111-035-003).

5. Results

The results are given in FIG. 2, which gives the anti-p24 IgG titers in the preimmune sera and the immune sera of the 6 rabbits (L1 to L6) having been given an injection either intradermally (ID) or subcutaneously (SC). The titer corresponds to the inverse of the dilution for which an OD approximately equal to 0.1 is obtained. The preimmune serum was taken at DO, before the injection of the immunogens, and the immune serum was taken at DO plus 4 months.

The results obtained show that the immunization with the PLA/p24 particles of the invention gives good titers in all the animals, irrespective of whether the antigen was administered subcutaneously or intradermally. However, in the model chosen, intradermal administration appears to be slightly better than subcutaneous administration. It may be noted that the titers obtained with the immunization of Freund's/p24 are substantially comparable to those obtained with a PLA/p24 immunization ($2 \times 10^7$ versus $5 \times 10^6$). The PLA/p24 microparticles can therefore be used to induce a polyclonal serum in rabbits.

EXAMPLE 7: IMMUNIZATION OF MACAQUES WITH THE PLA/P24 MICROPARTICLES OF THE INVENTION

1. Animal Model

The immunization experiments were carried out on cynomolgus macaques housed at the CEA.

2. Immunogens Administered

In this experiment, the PLA/p24 microparticles of the invention prepared as indicated in example 1, point 2 above, were used.

3. Immunizations

Two cynomolgus macaques were immunized with an injection of PLA/p24 (500 µg per animal administered IM), followed by an identical booster 6 weeks later. A third injection is given under the same conditions 6 months later.

4. Monitoring of the Appearance of the Anti-p24 Humoral Response

In order to follow the appearance of the anti-p24 antibodies, blood samples were taken from the macaques at weeks 0 (the day of the primer immunization), 2, 4, 6 (the day of the booster injection), 8, 10 and 12. The presence of the anti-p24 antibodies was then tested using the ELISA assay similar to that described in example 3, point 4 above, with the exception that the visualizing conjugate was replaced with a horseradish peroxidase-conjugated AFFINIPURE mouse anti-human IgG Fc gamma fragment antibody (H+L, Jackson Immunoresearch, Cat no. 209-035-098). The same ELISA format was also used to analyze the IgG subclasses present, using anti-human IgG1 (Cat no. 05-3320, Zymed), anti-human IgG2 (Cat no. 05-0520, Zymed), anti-human IgG3 (Cat no. 05-3620, Zymed) and anti-human IgG4 (Cat no. 05-3820, Zymed) horseradish peroxidase-conjugated antibodies.

5. Monitoring of the Appearance of the Anti-p24 Cellular Response by ELISPOT

This procedure makes it possible to determine the number of cells secreting interferon gamma (IFN-gamma) in response to an antigenic stimulation at a final concentration of 5 µg/ml for 48 h. This procedure was used successfully with freshly isolated peripheral blood mononuclear cells (PBMCs), PBMCs cryoconserved beforehand, T lymphocytes lines derived from PBMCs stimulated in vitro and from PBMCs pre-depleted of CD4+ cells (using an anti-CD4 antibody) or of CD8+ cells (using an anti-CD8 antibody). The CD4+ or CD8+ cell sorting was carried out using the MACS reagents, CD4 microbeads (Cat no. 130-091-102) and CD8 microbeads kit (Cat no. 130-091-112) from Miltenyi Biotec, according to the manufacturer's instructions.

The PMA-ionomycin couple (PMA for Phorbol Myristate Acetate), which mimics the effect of an antigenic activation of T lymphocytes, was used as a positive control.

96-well ELISPOT plates with PVDF membranes (Multiscreen, Millipore) were coated with the anti-macaque IFN gamma monoclonal antibody, clone GZ-4 (Mabtech, ref: 3420M-3) at 1 µg/ml in sterile PBS, overnight at +4° C. The plates were then washed and saturated. In parallel, PBMCs were isolated from the blood samples on a Ficoll gradient, according to the usual techniques. $10^5$ cells in 100 pl of culture medium/well and the antigen source in 100 µl of culture medium/well were deposited. According to the experiments, the antigen source is either the p24 protein, or a pool of gag peptides as defined hereinafter, for which it was verified beforehand that they make it possible to obtain a positive response in ELISPOT. In order to produce positive controls for stimulation, $4\times10^3$ cells in 200 pl of culture medium were deposited/well containing 50 ng/ml of PMA and 500 ng/ml of ionomycin. The plates were then incubated for 24 h at 37° C. in a humid atmosphere at 5% $CO_2$, and then washed with PBS. The remaining cells were then lysed using a treatment with ice-cold water for 10 minutes, and the plates were again washed. The visualizing antibody, the biotinylated monoclonal directed against human IFN-gamma, clone 7-B6-1 (Mabtech, ref: 3420-6) was then added at 0.1 µg/well (incubation for 2 h at 37° C. or overnight at 4° C.). The spots were visualized by adding extravidin-alkaline phosphatase and the 5-bromo-4-chloro-3-indolyl phosphate/nitro blue tetrazolium (BCIP/NBT) substrate. The sequences of the gag peptides used are as follows:

```
                            (SEQ ID No. 12)
EQIGWMTNNPPIPVG (SEQ ID No. 13)
WMTNNPPIPVGEIYK (SEQ ID No. 14)
NPPIPVGEIYKRWII (SEQ ID No. 15)
PVGEIYKRWIILGLN (SEQ ID No. 16)
IYKRWIILGLNKIVR (SEQ ID No. 17)
WIILGLNKIVRMYSP (SEQ ID No. 18)
GLNKIVRMYSPISIL (SEQ ID No. 19)
IVRMYSPTSILDIRQ (SEQ ID No. 20)
YSPTSILDIRQGPKE (SEQ ID No. 21)
SILDIRQGPKEPFRD
```

```
                            (SEQ ID No. 22)
IRQGPKEPFRDYVDR (SEQ ID No. 23)
PKEPFRDYVDRFYKT (SEQ ID No. 24)
FRDYVDRFYKTLRAE (SEQ ID No. 25)
VDRFYKTLRAEQASQ (SEQ ID No. 26)
YKTLRAEQASQEVKN (SEQ ID No. 27)
RAEQASQEVKNWMTE (SEQ ID No. 28)
ASQEVKNWMTETLLV (SEQ ID No. 29)
VKNWMTETLLVQNAN (SEQ ID No. 30)
MTETLLVQNANPDCK (SEQ ID No. 31)
LLVQNANPDCKTILK (SEQ ID No. 32)
NANPDCKTILKALGP
```

6. Results 6.1 Demonstration of the ELISPOT Responses

The results of the IFN-gamma ELISPOT assays for the two macaques (M1 and M2) having been given the PLA/p24 preparation, and the PBMCs of which were stimulated, are reproduced in FIG. 3, which represents histograms (mean of 4 replicates +/−standard deviations) giving the number of spots per million cells, obtained as a function of the days post-immunization, after stimulation without antigen (medium, negative control, solid histogram), after stimulation with p24 (hashed histogram) or after stimulation with the PMA-ionomycin couple. The arrows under each graph represent the moment at which the injections were given (D0 and D+6 weeks).

These results demonstrate that the PLA/p24 microparticles of the invention make it possible to induce an IFN-gamma ELISPOT response in the two animals tested. The first monkey (M1) only develops a specific response after the second injection, whereas the second animal (M2) has already developed a response at the first sample tested, after the first injection. In both cases, the effect of the booster injection is very significant (boost effect) since the ELISPOT responses obtained are high. Furthermore, the responses obtained are relatively long-lasting, given the fact that a non-replicative immunogen is involved; the responses remain significant approximately 40 days after the second injection.

6.2 Nature of the ELISPOT Responses

The nature of the ELISPOT responses makes it possible to demonstrate what types of effector immune cells, CD4+ or CD8+, are responsible for the IFN-gamma secretion measured.

The results are given in FIG. 4, which represents histograms giving the number of spots obtained by ELISPOT after stimulation either with the p24 protein (solid histograms), or with the peptides (hashed histograms), in the total PBMC fraction, the total PBMC fraction in the presence of the anti-CD4 antibody, the CD4+-depleted PBMC fraction (CD4− PBMC) and the corresponding CD4+-enriched fraction (CD4+ PBMC), and also the CD8+-depleted PBMC fraction (CD8− PBMC) and the corresponding CD8+-enriched fraction (CD8+ PBMC). It should be noted that the amount of cells obtained in the M1 monkey was not sufficient to carry out the depletion experiments with the anti-CD8 antibody.

The results obtained in FIG. 4 show that the secretion of the IFN-gamma cytokine is carried out by both the CD4− fraction and the CD8− fraction of the peripheral blood mononuclear cells. Furthermore, there is no ELISPOT response in the presence of an anti-CD4 antibody or of an anti-CD8 antibody (positive sorting fractions), indicating that each of these antibodies interferes with the immune response. This experiment therefore makes it possible to conclude that the IFN-gamma secretion observed is mediated by both CD4+ effector cells and CD8+ effector cells. Furthermore, this observation is valid irrespective of the nature of the antigenic stimulation used, p24 protein or pool of gag peptides. It is important to underline that this is the first time that a microparticle-based formulation has made it possible to induce, in primates, a CD8+ response specific for the antigen of interest.

6.3 Analysis of the Humoral Response

At the same time as the analysis of the cellular responses on the PBMCs, we also analyze the humoral response on the sequential sera obtained from the monkeys. Among the two animals, only the M2 monkey developed an antibody response, which reached an anti-p24 IgG titer of approximately $10^5$ following the second injection. The M1 monkey did not develop a significant antibody response after two injections of PLA/p24, the titer remaining less than $10^3$. This result is not very surprising because, during the analysis of the cellular responses, we were able to demonstrate that the M1 monkey was a poor responder, requiring an additional injection compared with the M2 monkey in order to develop an immune response.

The results of the ELISA assay with the M2 monkey are given in FIG. 5, which represents histograms giving the anti-p24 IgG titer in the M2 monkey as a function of the days on which the sequential sera were taken. These results show, firstly, that it is possible to induce specific antibody responses in macaques with the PLA/p24 microparticles of the invention and, secondly, that it is very probably necessary to add one or two additional injections to the protocol that we used in order to be certain of inducing a response even in less effective responders.

6.4 Conclusion

All these experiments carried out in the cynomolgus macaque model have made it possible to show that the microparticles of the invention make it possible to induce good immune responses in a nonhuman primate, with CD4+, CD8+ cellular responses and antibody responses.

EXAMPLE 8: IMMUNIZATION OF MICE WITH DENDRITIC CELLS SENSITIZED WITH THE PLA/P24 MICROPARTICLES OF THE INVENTION

1. Animal Model

The immunization experiments were carried out on female CBA/J ($H-2^k$) mice 6 to 8 weeks old at the time of the first immunization.

2. Immunogens Administered

In this experiment, the SRDC ($H-2^k$) murine spleen cell line was used in order to transport the various immunogens to be tested. This dendritic cell line was sensitized for 12 h with one of the following immunogens: PLA/p24 microparticles of the invention prepared as indicated in example 1, point 2 (at 10 µg/ml of p24/PLA in terms of p24 equivalent), PLA-OVA microparticles, prepared in the same way, which will serve as a negative control, or p24 protein.

3. Immunizations

The mice were divided up into 4 batches of 6 animals. Each mouse received $5 \times 10^5$ sensitized SRDC cells at 0, 2 and 4 weeks, subcutaneously. The 4 batches of mice received either nonsensitized cells (negative control), or cells sensitized with the PLA/p24 microparticles or PLA/OVA microparticles (microparticle negative control) or the p24 protein.

4. Monitoring of the Appearance of the Anti-p24 Humoral Response

In order to monitor the appearance of the anti-p24 antibodies, blood samples were taken from the mice every 10 days after immunization. The presence of the anti-p24 antibodies was then tested using the ELISA assay similar to that described in the preceding examples.

5. Results

The analysis of the humoral response is presented in FIG. 6, which represents histograms that give the OD value obtained by ELISA in the preimmune serum, in the serum after the $1^{st}$ immunization, in the serum after the second immunization and in the serum after the $3^{rd}$ immunization, of the mice sensitized either with the negative control (Ct1 and Ct2), or with the p24 protein (p24-1 and p24-2), or with the microparticle negative control (NanoOval and NanoOva2) or with the microparticles of the invention (Nanop24-1 and Nanop24-2).

The results show that the injection of SRDC cells induces antibodies only when the SRDCs are sensitized with the PLA-p24 microparticles. The sensitization with the soluble p24 protein does not make it possible to obtain an immune response.

6. Study of the Cellular Response

The study was carried out using both splenic and mucosal lymphocytes isolated from the mice. The analysis of the stimulated T lymphocyte subpopulations was carried out using lymphoproliferation and cytokine secretion assays so as to evaluate their ability to respond to the antigen, two weeks after the final immunization.

For the lymphoproliferation assays, the T lymphocytes isolated from the spleen and from the mucosal lymph nodes were placed in culture for 5 days in complete culture medium in the presence of various concentrations of the antigen of interest, and then radiolabeled with $^3H$ thymidine for 18 h. The level of thymidine incorporation corresponds to the degree of the lymphoproliferative response.

For the cytokine secretion assays, the T lymphocytes isolated from the spleen and from the mucosal lymph nodes were placed in culture for 3 days in complete culture medium in the presence of various concentrations of the antigen of interest, and then the cytokine secreted into the culture supernatant were assayed using commercial ELISA kits.

7. Results

Table 4 below gives a summary of the results obtained.

TABLE 4

| Groups of mice | Number of mice having developed an antibody (IgG) response after the $3^{rd}$ injection | Lymphoproliferation Stimulation index Spleen-lymph node | IFN-gamma secretion |
|---|---|---|---|
| Control | 0/2 | 1-1 | No |
| SRDC-p24 | 0/2 | 1-1 | No |
| SRDC-PLA-Ova | 0/2 | 1.4-1.4 | No |
| SRDC-PLA-p24 | 2/2 | 2.8-2.2 | +spleen, ++lymph node |

As above, the results show that the SRDC-PLA-p24 group is the only group for which it is possible to demonstrate a specific immune response. The stimulation index is 2.8 for the cells isolated from the spleen and 2.2 for those isolated from the mesenteric lymph nodes. For the other groups, there is no increase in the stimulation index or it is not significant. Similarly, the SRDC-PLA-p24 group is the only group which makes it possible to induce secretion of IFN-gamma, which is a Th1-type cytokine. This secretion in the presence of the antigen can be demonstrated using both the spleen cells and those of the mesenteric lymph nodes.

8. Conclusion

All these experiments have enabled us to show that it is also possible to use the PLA-p24 microparticles in order to sensitize dendritic cells with an antigen of interest, in this case p24. Although administration of the SRDCs, when they are loaded with the PLA-p24s, makes it possible to induce both cellular and humoral specific responses, the SRDCs sensitized with the soluble p24 do not make it possible to induce anti-p24 responses. Thus, the PLA microparticles can also be used successfully in immunotherapy applications based on the transfer of dendritic cells sensitized in vitro.

When the antigen of interest cannot be loaded into the dendritic cells in its soluble form, the PLA microparticles carrying the antigen can be used to facilitate its uptake by the dendritic cells. The use of the microparticles of the invention makes it possible to considerably enhance the specific immune responses obtained.

EXAMPLE 9: IMMUNIZATION OF MICE WITH THE PLA/NS3 HELICASE MICROPARTICLES OF THE INVENTION: EARLY AND LOCALIZED CELLULAR RESPONSE

1. Animal Model

The immunization experiments were carried out on female BALB/c ($H-2^d$) mice 6 to 8 weeks old at the time of the first immunization.

2. Immunogens Administered

In this experiment, 5 mice per immunization group were used: the NS3 helicase genotype 1b protein (NS3h) alone, the PLA/NS3h microparticles of the invention prepared by dialysis (PLADYS) as indicated in example 1, point 4 above, the PLA/NS3h microparticles of the invention prepared by solvent displacement (PLADDS) as indicated in example 2, point 2 above, and also the NS3h-Alum (Pierce) composition prepared in the form of an emulsion and known to be an adjuvant in commercial vaccines (positive control).

3. Immunizations

The mice received one dose (100 μg) of the immunogens described in point 2 above, subcutaneously into the plantar footpad.

The animals were sacrificed 10 days after the first injection and the popliteal lymph nodes were removed for immunological analysis.

4. Immunological Analyses

The early and localized NS3h protein-specific dose-response cellular response was investigated as follows:

Proliferation of the Popliteal Lymph Node Cells after Stimulation with Various Concentrations of the NS3h Protein— the popliteal lymph node cells were stimulated in the presence of 0, 0.1, 0.3 and 1 μl of the NS3h protein for 3 days. The cells were pulsed for 18 h with tritiated thymidine, which incorporates into the DNA of the cells undergoing proliferation.

Following the pulse, the cells were harvested on a membrane which retains the DNA and makes it possible to eliminate the nonincorporated labeled thymidine by washing. The more the cells proliferate in response to the specific stimulus, the more the DNA is labeled; in other words, the greater the cellular response against the NS3h immunogen.

5. Results

The results of the proliferation of the popliteal lymph node cells after stimulation with the NS3h protein are indicated in FIG. 7 representing the graphs giving the relative proliferation index (RPI) specific to the NS3h protein, corresponding to the ratio of cpm (counts per minute) obtained for each concentration of NS3h (0, 0.1, 0.3 and 1 μM) relative to the zero concentration of the NS3h protein, as a function of the amount of NS3h used for the restimulation for the cell proliferation assay, in mice having received NS3h-PBS (PBS), microparticles of the invention prepared by dialysis (DYS), microparticles of the invention prepared by solvent displacement (DDS) and the NS3h-Alum composition.

This graph shows a cellular response specific for the NS3h protein when the PLA/NS3h microparticles prepared by solvent displacement (DDS) and the PLA/NS3h microparticles prepared by dialysis (DYS) are injected. The specific cellular responses of the mice injected with the PLADDS/NS3hs of the invention are greater than those obtained with the PLADYS/NS3hs of the invention, the positive control (Alum/NS3h) and the PBS/NS3h control for all the concentrations of NS3h antigens tested (PLADDS/NS3h>PLADYS/NS3h>Alum/NS3h=PBS/NS3h).

The results show that enhanced cellular proliferative responses are obtained with the PLADDS/NS3h and PLADYS/NS3h microparticles of the invention, compared with the NS3h protein alone or adjuvanted with Alum.

EXAMPLE 10: IMMUNIZATION OF MICE WITH THE PLA/NS3 HELICASE MICROPARTICLES OF THE INVENTION: LOCALIZED AND SYSTEMIC CELLULAR RESPONSE AND INHIBITION OF THE SYSTEMIC CELLULAR RESPONSE WITH ANTI-$CD4^+$ ANTIBODIES

1. Animal Model

The immunization experiments were carried out on female BALB/c ($H-2^d$) mice 6 to 8 weeks old at the time of the first immunization.

2. Immunogens Administered

In this experiment, 5 mice per immunization group were used: the NS3 helicase genotype 1b protein (NS3h) alone, the PLA/NS3h microparticles of the invention prepared by dialysis (PLADYS) as indicated in example 1, point 4 above, the PLA/NS3h microparticles of the invention prepared by solvent displacement (PLADDS) as indicated in example 2, point 2 above, and also the NS3h-Alum (Pierce) composition prepared in the form of an emulsion and known to be an adjuvant in commercial vaccines (positive control).

3. Immunizations

The mice received 2 doses (100 pig) of the immunogens described in point 2 above, the first dose having been given subcutaneously into the plantar footpad at day 0 and the second subcutaneously at the base of the tail at day 7.

The animals were sacrificed 7 days after the second injection and the popliteal lymph nodes and the spleen were removed for immunological analysis.

4. Immunological Analyses

The NS3h protein-specific dose-response cellular response localized in the popliteal lymph nodes and systemic in the spleen was investigated as follows:

Proliferation of the Popliteal Lymph Node Cells after Stimulation with Various Concentrations of the NS3h Protein— the cells of the popliteal lymph nodes and of the spleen were stimulated in the presence of 0, 0.1, 0.3 and 1 µM of the NS3h protein for 3 days. After 3 days of culture, 50 µl of supernatant were removed. The cells were pulsed for 18 h with tritiated thymidine, which incorporates into the DNA of the cells undergoing proliferation. Following the pulse, the cells were harvested on the membrane that retains the DNA and that makes it possible to eliminate the nonincorporated labeled thymidine by washing. The more the cells proliferate in response to the specific stimulus, the more the DNA is labeled; in other words, the greater the cellular response against the NS3h immunogen.

It was sought to inhibit the cellular response with anti-$CD4^+$ antibodies (GK1.5; American Type Culture Collection (ATCC)) in the cells originating from the spleen as follows:

(i) Inhibition, with the Anti-$CD4^+$ Antibody, of the Proliferation of the Spleen Cells after Stimulation with $1_4$M of the NS3h Protein— the spleen cells were stimulated in the presence of 1 µM of the NS3h protein and incubated with 10 µg of anti-$CD4^+$ antibody for 3 days. The cells were pulsed for 18 h with tritiated thymidine, which incorporates into the DNA of the cells undergoing proliferation. Following the pulse, the cells were harvested on a membrane that retains the DNA that makes it possible to eliminate the nonincorporated labeled thymidine by washing. The more the cells proliferate in response to the specific stimulus, the more the DNA is labeled; in other words, the greater the cellular response against the NS3h immunogen.

(ii) Assaying of Interferon γ— the interferon γ was assayed using the BD™ Cytometric Bead Array kit, Mouse Th1/Th2 Cytokine CBA (BD Biosciences, Cat. No. 551287). Five populations of beads with distinct fluorescence intensities were coated with capture antibodies specific for IL-2, IL-4, IL-5, IFN-gamma, and TNF-alpha proteins. The five populations of beads were mixed together to form the CBA, which is resolved in the FL3 channel of a flow cytometer such as the BD FACScan™ Coule Cytometer. The cytokine capture beads were mixed with phycoerythrin-conjugated detection antibodies, and then incubated according to the supplier's recommendations. The sample data acquisition using the flow cytometer to produce the results was carried out using the BD CBA analytical software.

5. Results 5.1 Localized and Systemic Cellular Response

The results of the proliferation of the spleen cells after stimulation with the NS3h protein are indicated in FIG. 8, representing the graphs giving the relative proliferation index (RPI) specific to the NS3h protein as a function of the amount of NS3h used (in µM) in mice having received NS3h-PBS (PBS), microparticles of the invention prepared by dialysis (DYS), microparticles of the invention prepared by solvent displacement (DDS) and the NS3h-Alum composition (Alum), in the cells of the popliteal lymph nodes for the localized cellular response (FIG. 8A) and in the cells of the spleen for the systemic cellular response (FIG. 8B).

These results demonstrate a cellular response that is systemic (spleen cells—FIG. 8B) and specific for the NS3h protein at 1 µM with the PLA/NS3h microparticles of the invention prepared by solvent dispersion (DDS) and the PLA/NS3h microparticles prepared by dialysis (DYS). The specific cellular responses of the mice having received the PLADDS/NS3h and PLADYS/NS3h of the invention are greater than those obtained with the positive control (Alum/NS3h) and the PBS/NS3h control (PBS) (PLADDS/NS3h and PLADYS/NS3h>>>Alum/NS3h=PBS/NS3h).

5.2 Inhibition of the Systemic Cellular Response with the Anti-CD4 Antibody.

The results are indicated in FIG. 9, which represents histograms giving the cellular proliferation index (RPI) as a function of the immunogens used in mice, i.e. NS3h-PBS (PBS), microparticles of the invention prepared by dialysis (DYS), microparticles of the invention prepared by solvent displacement (DDS) and the NS3h-Alum composition (Alum), in the spleen cells without stimulation (0), after stimulation with NS3h protein (1) or after stimulation with protein and anti-CD4+ antibody (1+aCD4).

The results show that the systemic cellular response is inhibited by at least a factor of 5 in the presence of the anti-CD4+ antibody, suggesting that the NS3h protein-specific response is of the Th2 type.

5.3 Supplementary Results

At the third day of proliferation after stimulation with the NS3h protein, interferon gamma (IFN-gamma) secretion was observed under all the conditions used, which secretion is decreased with the anti-$CD4^+$ antibody.

The results of the IFN-gamma assay at the third day after stimulation with the NS3h protein are given in table 5 below:

TABLE 5

| | Type of stimulation | Interferon gamma assay pg/ml |
|---|---|---|
| PBS/NS3h | 1 µM of NS3h | 316 |
| | 1 µM of NS3h + anti-CD4+ | 60 |
| PLADDS/NS3h | 1 µM of NS3h | 556 |
| | 1 µM of NS3h + anti-CD4+ | 196 |
| PLADYS/NS3h | 1 µM of NS3h | 606 |
| | 1 µM of NS3h + anti-CD4+ | 249 |
| Alum/NS3h | 1 µM of NS3h | 583 |
| | 1 µM of NS3h + anti-CD4+ | 144 |

EXAMPLE 11: IMMUNIZATION OF MICE WITH THE PLA/NS3 HELICASE MICROPARTICLES OF THE INVENTION: HUMORAL RESPONSE

1. Animal Model

The immunization experiments were carried out on female BALB/c ($H-2^d$) mice 6 to 8 weeks old at the time of the first immunization.

2. Immunogens Administered

In this experiment, 5 mice per immunization group were used, the NS3 helicase genotype 1b protein (NS3h) alone, the PLA/NS3h microparticles of the invention prepared by dialysis (PLADYS) as indicated in example 1, point 4 above, the PLA/NS3h microparticles of the invention prepared by solvent displacement (PLADDS) as indicated in example 2, point 2 above, and also the NS3h-Alum (Pierce) composition prepared in the form of an emulsion and known to be an adjuvant in commercial vaccines (positive control).

3. Immunizations

The mice received 3 doses (50 µg) of the immunogens described in point 2 above, subcutaneously at the base of the tail at 0, 2 and 4 weeks. The sera were taken at day 13, day 27 and day for the analyses of the specific humoral response against the NS3h protein using an ELISA assay as indicated hereinafter.

The animals were sacrificed at 10 days after the first injection and the popliteal lymph nodes were removed for immunological analysis.

4. Immunological Analyses

The early and localized NS3h protein-specific humoral response was investigated as follows:

Qualitative and Quantitative Humoral Response Against the NS3h Protein— a blood sample was taken from the mice before the first injection (DO), and at D13, D27 and D45. The presence of the specific anti-NS3h antibodies, the antibody titer and the immunoglobulin isotypes (IgG, IgG1, IgG2a) were determined by ELISA. The microtitration plates were sensitized with the NS3h protein and the specific antibodies against the NS3h protein that were present in the serum of immunized mice were visualized using peroxidase-labeled goat anti-mouse IgG serum (H+L, Jackson Immunoresearch, Cat no. 115-035-062). For the determination of the antibody titer, the immunized mice sera were serially diluted. For the determination of the isotyping, the reaction was visualized using peroxidase-labeled goat anti-mouse IgG1 serum (Southern Biotechnology Associates Inc., Cat no. 1070-05, Birmingham, Ala., USA), and a peroxidase-labeled goat anti-mouse IgG2a antibody (Interchim, UPB 90520). The IgG2a/IgG1 isotype ratio, which makes it possible to interpret the IFN-gamma/IL-4 (respectively, Th1-Th2) tendency of the immune response was also determined.

5. Results

The results of the specific anti-NS3h total IgG antibody titer at day 30 and day 45 are given in table 6 below:

TABLE 6

| | Specific anti-NS3h antibody titer | |
| --- | --- | --- |
| | Day 30 | Day 45 |
| NS3h | $3.3 \times 10^3$ | $4.5 \times 10^4$ |
| PLADYS/NS3h | $3.5 \times 10^4$ | $2.6 \times 10^5$ |
| Freund's adjuvant/NS3h | $7.1 \times 10^4$ | $1.9 \times 10^5$ |

The results demonstrate that the bonding of the NS3h protein to the PLAs makes it possible to enhance the antibody (total IgG) titers by approximately 1 log relative to the titer obtained with the NS3h protein alone. Moreover, the titers obtained are also comparable to those obtained with the Freund's adjuvant/NS3h formulation.

The use of the PLA/NS3h microparticles makes it possible to obtain an essentially IgG1 antibody response specific for the NS3h protein, suggesting that the response is of the Th2 type.

EXAMPLE 12: ACTION OF THE PLA/NS3HS DURING THE DIFFERENTIATION OF MONOCYTES TO DENDRITIC CELLS

This study consists in studying the effect on antigen-presenting cells of the NS3h protein adsorbed onto PLA nanoparticles. To do this, the procedure is carried out in the presence of dendritic cells generated using monocytes isolated from human peripheral blood and differentiated.

Analysis of the expansion of costimulatory molecules makes it possible to determine whether dendritic cells that are immature at the start (DCi) enter into a process of maturation.

The ability of the potential adjuvant and of the PLA-NS3h formulation to promote the differentiation and maturation of monocytes into dendritic cells is also tested. This study enables us to understand more clearly their role in cell mediation, which is essential at the interface between innate and adaptive immunity. The screening is carried out by means of successive steps of analysis of phenotypic markers of differentiation and of maturation and by analysis of the profile of cytokines produced. The analysis of the cytokine production makes it possible to identify whether the PLA-NS3 formulation induces a Th1 and/or Th2 profile.

1. Purification of Monocytes from Human Peripheral Blood

The monocytes were isolated from normal human peripheral blood (recovered at the Etablissement Francais du Sang [French bloodbank] in Lyon) by centrifugation on a Ficoll and Percoll (Amersham Biosciences) gradient. The Ficoll makes it possible to create a density gradient while at the same time conserving the integrity of the cells and their function. After centrifugation, the red blood cells and the polymorphonuclear cells that are more dense than the Ficoll are at the bottom of the tube. The PBMCs (peripheral blood mononuclear cells) comprising lymphocytes and monocytes remain at the interface between the plasma and the Ficoll. They are then purified on a Percoll gradient. After centrifugation, the lymphocytes, that are more dense than the Percoll, are in the pellet, whereas the monocytes remain at the interface between the medium and the Percoll.

The monocytes were incubated with the mixture of antibodies (Ab) indicated hereinafter, in order to eliminate the remaining contaminants by depletion of T lymphocytes (mouse anti-CD3 Ab OKT3, ATCC, Rockville, Md., USA, directed against T lymphocytes), of B lymphocytes (mouse anti-CD19 Ab hybridoma 4G7, directed against B lymphocytes), of red blood cells (mouse anti-glycophorin A Ab, Immunotech) and of NK cells (mouse anti-CD56 Ab NKH1, Immunotech, directed against Natural Killer cells) and using magnetic beads (DYNAL). The Dynal beads are small magnetic beads coated with sheep antibodies directed against mouse antibodies. These antibodies will bind the mouse Ab/cell complexes and then, after the cell suspension has been passed over a magnetized carrier, the remaining cells will only be monocytes.

The depletion was verified by FACScan (Becton Dickinson) flow cytometry analysis.

The cell suspension was analyzed by isolated passage of the cells through a liquid matrix. The passage of these cells through a light beam results in two types of scattering referred to as small angle (Forward scatter-FS) and large angle (Side scatter—SS), which represent the two cellular parameters taken into account, the size (scattering) and the granulometry (refraction) of the cells. The use of antibodies coupled to fluorochromes (FITC: Fluorescein IsoThioCyanate read on the X-axis FL1 and PE: PhycoErythrin read on the Y-axis in FL2) that are laser-excitable allows detectable fluorescence emission. An electrical signal amplification and analog-digital converter system allows the data to be computer-formatted.

The cells were labeled with various types of antibodies:
Anti-CD14 Ab labeled with FITC (monocyte specific)
Anti-CD3 Ab labeled with PE (LT specific)
Anti-CD56 Ab PE (NK cells)
Anti-CD20 Ab PE (LB specific).
The contaminant level is less than 10%.

The monocytes were subsequently placed in culture (day 0) in 24-well plates at a rate of $1 \times 10^6$ cells/ml in RPMI 1640 medium (Gibco), 2 mM of L-glutamine (Life Technologies), 10 mM Hepes (Life Technologies), 40 ng/ml of gentamycin (Life Technologies)+10% decomplemented fetal calf serum, and in the presence of GM-CSF (40 ng/ml) (Granulocyte Macrophage Colony Stimulating Factor) and recombinant human IL-4 (250U/ml). The GM-CSF and the IL-4 allow differentiation of the monocytes into immature dendritic cells.

2. Phenotypic Analysis of the Cells

At the 5$^{th}$ day of differentiation, various tests were applied to the cells:

LPS from 250 to 2000 pg/ml→LPS (lipopolysaccharide) is a component of the bacterial membrane and is recognized as a danger signal by DCis, systematically allowing their maturation. A range of LPS concentrations was realized in each of the assays in order to compare the degrees of maturation.

A dose-response was carried out for the NS3h alone, the particles alone and the PL/NS3h particles.

NS3h from 1 to 50 µg/ml→control for ensuring that the protein alone does not induce any maturation.

PLA from 0.01 to 1 mg/ml→test to determine whether the PLAs have an adjuvant effect.

PLA/NS3h from 10 to 100 µl→test to determine whether the PLAs have an adjuvant effect in the presence of the NS3h protein.

At the 6$^{th}$ day, 200 µl of the supernatant were conserved at −80° C. for assaying the cytokines. The cells were subsequently collected and then washed.

Various control labelings were carried out:

a control isotype labeling IgG1-FITC/IgG2a-PE: IgGs are capable of binding nonspecifically to cells possessing an Fc fragment receptor. This labeling therefore makes it possible to be sure of the specificity of the reaction and to eliminate the nonspecific fluorescence from the various assays. The use of IgG1 and of IgG2a is related to the fact that the anti-CD antibodies used are also of this type;

a CD14-FITC (specific for monocytes)/CD1a-PE (specific for immature dendritic cells) labeling makes it possible to be sure that the differentiation has correctly functioned.

The phenotype was subsequently determined by specific labeling of the mature dendritic cells with:

anti-CD80 FITC Ab/anti-CD86 PE Ab
anti-HLA-DR FITC Ab/anti-CD83 PE Ab
anti-CD40 PE Ab.

3. Implementation of the Dendritic Cell Maturation Protocol

The formulations were brought into contact with the immature dendritic cells in order to judge the ability of the PLA/NS3h particles to generate mature dendritic cells (adjuvant effect).

The assays carried out were as follows:
LPS range: 250-300-400-500-750-1000-2000 pg
NS3h: 1-10-25-50 µg
PLA particles: 0.05-0.1-0.5-1 mg
PLA/NS3h particles: 0.24 mg DYS/10 µg NS3h (10 µl)-0.6 mg/25 µg (25 µl)-1.2 mg/50 µg (50 µl)-2.4 mg/100 µg (100 µl).

4. Results

The NS3h protein gives no positive labeling.

The PLA DYS particles alone, added at D5 to DCis, make it possible to obtain a maturation phenotype (DCm CD83+, CD86+, CD40+). A dose-response effect on cell maturation was observed.

The PLA/NS3h particles give very advantageous results. Specifically, it can be noted that the degree of activation of maturation is substantial. Right from the assay at 10 µl (0.24 mg PLA/10 µg helicase), maturation can be observed. The PLA/NS3hs added to DCis induce the expression of all the activation markers (CD83+, CD86+, CD80+, HLA-DR+, CD40+).

The assay at 100 µl was carried out in the knowledge that it is in large excess in the conditions used in vitro.

In conclusion, the PLA formulations have an adjuvant effect on the HCV NS3h protein since they make it possible to obtain mature dendritic cells.

EXAMPLE 13: OBTAINING MONOCLONAL ANTIBODIES WITH THE PLA/P24 MICROPARTICLES OF THE INVENTION

1. Animal Model

The immunization experiments were carried out on female BALB/c (H-2$^d$) mice 6 to 8 weeks old at the time of the first immunization.

2. Immunogens Administered

In this experiment, the PLA/p24 microparticles of the invention prepared as indicated in example 1, point 2, and also the p24-Freund's adjuvant (Sigma) composition prepared in the form of a water-in-oil emulsion, and which is known to have a good immunogenic capacity (positive control), were used.

3. Immunizations

The mice received 3 successive doses of 10 µg of the immunogens described in point 2 above, at 0, 2 and 4 weeks. All the injections were given subcutaneously. At D68 after the first injection, the humoral responses were restimulated with an intravenous injection of 50 µg of p24.

4. Monitoring of the Appearance of the Anti-p24 Humoral Response

In order to monitor the appearance of the anti-p24 antibodies, blood samples were taken regularly from the mice. The presence of the anti-p24 antibodies is then tested using the ELISA assay similar to that described in example 2, point 4. However, the visualizing conjugate is replaced with an alkaline phosphatase-conjugated AffiniPure goat anti-mouse IgG antibody (H+L, Jackson Immunoresearch, Cat no. 115-055-146).

5. Obtaining Monoclonal Antibodies

Three days after the final injection, a mouse of the PLA-p24 group was sacrificed; the blood and the spleen were taken. The splenocytes obtained from the spleen were placed in culture with Sp2/0-Ag14 myeloma cells so that they would fuse and become immortalized, according to the protocol described by Köhler and Milstein (Köhler, G. and Milstein, C., 1975, Nature, 256:495-497; Köhler, G. and Milstein, C., 1976, Eur. J. Immunol., 6:511-519). After an incubation period of 12-14 days, the supernatants of the hybridomas obtained were screened in order to determine the presence of anti-p24 antibodies using the ELISA assay described in point 4 of this example. The positive hybridoma colonies were subcloned twice according to the limiting dilution technique.

6. Results

The anti-p24 antibody titer in the serum of the mice was determined just before sacrifice, individually for each mouse.

The results are given in table 7 below.

TABLE 7

|  |  | PLA/p24 group |
| --- | --- | --- |
| Mouse 1 | dilution 1/8000 | >3.0 (saturating) |
|  | dilution 1/64000 | 0.5 |

TABLE 7-continued

| | | |
|---|---|---|
| Mouse 2 | dilution 1/8000 | >3.0 (saturating) |
| | dilution 1/64000 | 0.5 |
| Mouse 3 | dilution 1/2000 | >3.0 (saturating) |
| | dilution 1/8000 | 1.3 |
| Freund's/p24 group | | |
| Mouse 1 | dilution 1/8000 | >3.0 (saturating) |
| | dilution 1/64000 | 0.5 |
| Mouse 2 | dilution 1/8000 | >3.0 (saturating) |
| | dilution 1/64000 | 0.5 |
| Mouse 3 | dilution 1/2000 | >3.0 (saturating) |
| | dilution 1/8000 | 1.4 |

The titers obtained are comparable in the two groups. As monoclonal antibodies had already been obtained by Freund's/p24 immunization, we sought to determine whether the PLA/p24 immunogen, which makes it possible to induce comparable titers, will also make it possible to obtain monoclonal antibodies.

For this, a mouse of the PLA/p24 group (mouse 1) was sacrificed and the cells from its spleen were fused with myeloma cells. The hybridomas derived from the fusion were cloned by limiting dilution in 18 96-well plates. Screening of the hybridoma culture supernatants using an anti-p24 ELISA assay made it possible to identify 12 hybridoma clones which secrete a p24-specific antibody. The PLA/p24 microparticles can therefore also be used to obtain monoclonal antibodies.

What is claimed is:

1. Bioresorbable nonlamellar microparticles to which protein substances are bonded, consisting of poly(lactic acid),
   the microparticles being obtained by:
   (i) preparing, without stabilizer and without surfactant, said microparticles by a solvent displacement method; and
   (ii) bonding said protein substances to the microparticles obtained in step (i) without surfactant;
   wherein the microparticles to which are bonded the protein substances exhibit colloidal stability, and have a diameter in a range of 150 to 250 nm.

2. The bioresorbable nonlamellar microparticles according to claim 1, wherein the protein substance is an antigen of viral origin.

3. The bioresorbable nonlamellar microparticles according to claim 1, wherein the bonding of the protein substances to the microparticles is carried out by adsorption.

4. A pharmaceutical composition, comprising at least one bioresorbable microparticle according to claim 1.

5. The pharmaceutical composition according to claim 4, wherein the pharmaceutical composition is a vaccine.

6. The pharmaceutical composition according to claim 4, further comprising a pharmaceutically acceptable excipient.

7. A diagnostic composition comprising the bioresorbable microparticles according to claim 1.

8. Bioresorbable nonlamellar microparticles to which protein substances are bonded, comprising poly(lactic acid),
   wherein the microparticles exhibit colloidal stability, are devoid of stabilizer and surfactant, and have a diameter in a range of 150 to 250 nm.

* * * * *